(12) United States Patent
Madjunkova et al.

(10) Patent No.: US 11,814,682 B2
(45) Date of Patent: Nov. 14, 2023

(54) METHOD FOR PREIMPLANTATION GENETIC SCREENING OF EMBRYOS FOR DETECTION OF STRUCTURAL REARRANGEMENTS

(71) Applicant: REPROBIOGEN INC., Toronto (CA)

(72) Inventors: Svetlana Madjunkova, Toronto (CA); Clifford L. Librach, Toronto (CA)

(73) Assignee: REPROBIOGEN INC., Toronto (CA)

( * ) Notice: Subject to any disclaimer, the term of this patent is extended or adjusted under 35 U.S.C. 154(b) by 214 days.

(21) Appl. No.: 17/083,803

(22) Filed: Oct. 29, 2020

(65) Prior Publication Data

US 2022/0136052 A1  May 5, 2022

(51) Int. Cl.
*C12Q 1/6883* (2018.01)

(52) U.S. Cl.
CPC ..... *C12Q 1/6883* (2013.01); *C12Q 2600/156* (2013.01)

(58) Field of Classification Search
CPC .................................................. C12Q 1/6883
See application file for complete search history.

(56) References Cited

PUBLICATIONS

Hu, L. et al., Location of Balanced Chromosome-Translocation Breakpoints by Long-Read Sequencing on the Oxford Nanopore Platform, Front. In Genetics, vol. 10: 1313, pp. 1-10 (Year: 2020).*
Aoyama, N. et al. Trophectoderm biopsy for preimplantation genetic test and technical tips: A review, Reprod. Med. Biol., vol. 19, pp. 222-231 (Year: 2020).*
Wang, L. et al., Validation of Copy Number Variation Sequencing for Detecting Chromosome Imbalances in Human Preimplantation Embros, Biol. Reprod., vol. 91: 37, pp. 1-8 (Year: 2014).*
Oxford Nanopore Technologies White Paper (pp. 1-16 (Year: 2017).*
Magi, A. et al., Nano-Gladiator: real-time detection of copy number alterations from nanopore sequencing data, Bioinformatics, vol. 35, pp. 4213-4221 (Year: 2019).*
Chow, J.F.C. et al., Distinguishing between carrier and noncarrier embryos with the use of long-read sequencing in preimplantation genetic testing for reciprocal translocations, Genomics, vol. 112, pp. 494-500 (Year: 2020).*
Jain, m. et al., Nanopore sequencing and assembly of a human genome with ultra-long reads, Nature Biotechnol., vol. 36, pp. 338-345 plus online methods pp. 1-5, (Year: 2018).*
Aristidou et al., "Accurate Breakpoint Mapping in Apparently Balanced Translocation Families with Discordant Phenotypes Using Whole Genome Mate-Pair Sequencing," PloS One, Jan. 2017, vol. 12(1), e0169935, pp. 1-18.
Bar et al., "The Gene Encoding Disabled-1 (DAB1), the Intracellular Adaptor of the Reelin Pathway, Reveals Unusual Complexity in Human and Mouse," The Journal of Biological Chemistry, Feb. 2020, vol. 278(8), pp. 5802-5812.
Darwish and Magdi., "Artificial Shrinkage of Blastocoel Using a Laser Pulse Prior to Vitrification Improves Clinical Outcome," Journal of Assisted Reproduction and Genetics, Feb. 2016, vol. 33(4), pp. 467-471.
Garvin et al., "Interactive Analysis and Assessment of Single-Cell Copy-Number Variations," Nature Methods, Sep. 2015, vol. 12, pp. 1058-1060.
Halgren et al., "Risks and Recommendations in Prenatally Detected De Novo Balanced Chromosomal Rearrangements from Assessment of Long-Term Outcomes," American Journal of Human Genetics, Jun. 2018, vol. 1-14, pp. 1090-1103.
Handyside et al., "Karyomapping: A Universal Method for Genome Wide Analysis of Genetic Disease Based on Mapping Crossovers Between Parental Haplotypes," Journal of Medical Genetics, 2010, vol. 47, pp. 651-658.
Huang et al., "Signaling Through Disabled 1 Requires Phosphoinositide Binding," Biochemical and Biophysical Research Communications, 2005, vol. 331, pp. 1460-1468.
Li., "Minimap2: Pairwise Alignment for Nucleotide Sequences," Bioinformatics, 2018, vol. 34(18), pp. 3094-3100.
Li., "The Sequence Alignment/Map Format and SAMtools," Bioinformatics, Aug. 2009, vol. 25(16), pp. 2078-2079.
Madjunkova et al., "Non-Invasive Preimplantation Genetic Testing for Monogenic Diseases and Aneuploidies Using Cell Free Embryonic DNA," The American Society of Human Genetics (ASHG), San Diego, USA, Oct. 2018, Abstract 3007T, 2 pages.
Munne et al., "Outcome of Preimplantation Genetic Diagnosis of Translocations," Fertility and Sterility, Jun. 2000, vol. 73(6), pp. 1209-1218.
Seixas et al., "A Pentanucleotide ATTTC Repeat Insertion in the Non-Coding Region of DAB1, Mapping to SCA37, Causes Spinocerebellar Ataxia," American Journal of Human Genetics, Jul. 2017, vol. 101, pp. 87-103.
Stancu et al., "Mapping and Phasing of Structural Variation in Patient Genomes Using Nanopore Sequencing," Nature Communications, Nov. 2017, vol. 8, 1326, pp. 1-13.

(Continued)

*Primary Examiner* — Teresa E Strzelecka
(74) *Attorney, Agent, or Firm* — BORDEN LADNER GERVAIS LLP; Kathleen E. Marsman

(57) ABSTRACT

A method is described for determining carrier status of an embryo for a balanced chromosomal rearrangement (BCR) prior to implantation of the embryo. The method involves obtaining cells from the embryo from at least day 4 post in vitro fertilization; conducting long-read nanopore sequencing of the DNA of the cells and the BCR carrier parent to detect at least one breakpoint; preparing primers specific to the breakpoint; employing the primers in a polymerase chain reaction customized to the breakpoint (cBP-PCR) to determine whether the breakpoint is indicative of BCR; and determining on the basis of cBP-PCR whether the embryo status is BCR carrier or BCR noncarrier; and conducting Sanger sequencing to determine balance in the embryo. The method can assist BCR carrier parents to pursue reproductive technologies while preventing vertical transmission of a BCR to offspring.

13 Claims, 17 Drawing Sheets

(56) References Cited

PUBLICATIONS

Tan et al., "Single-Nucleotide Polymorphism Microarray-Based Preimplantation Genetic Diagnosis is Likely to Improve the Clinical Outcome for Translocation Carriers," Human Reproduction, 2013, vol. 28(9), pp. 2581-2592.

Treff et al., "SNP Array-Based Analyses of Unbalanced Embryos as a Reference to Distinguish Between Balanced Translocation Carrier and Normal Blastocysts," Journal of Assisted Reproduction and Genetics, May 2006, vol. 33(8), pp. 1115-1119.

Untergasser et al., "Primer3—New Capabilities and Interfaces," Nucleic Acids Research, Jun. 2012, vol. 40(15), e115, pp. 1-12.

Vermeesch et al., "Prenatal and Pre-Implantation Genetic Diagnosis," Nature Reviews Genetics, Oct. 2016, vol. 17, pp. 643-656.

Wang et al., "Preferential Selection and Transfer of Euploid Noncarrier Embryos in Preimplantation Genetic Diagnosis Cycles for Reciprocal Translocations," Fertility and Sterility, Oct. 2017, vol. 108(4), pp. 620-627.e4.

Wei et al., "Rapid Preimplantation Genetic Screening Using a Handheld, Nanopore-Based DNA Sequencer," Fertility and Sterility, Oct. 2018, vol. 110(5), pp. 910-916.e2.

Zhang et al., "The Establishment and Application of Preimplantation Genetic Haplotyping in Embryo Diagnosis for Reciprocal and Robertsonian Translocation Carriers," BMC Medical Genomics, Oct. 2017, vol. 10, 60, pp. 1-9.

\* cited by examiner

Read name = derived
Read length = 3,405bp
Reference span = chr8:139,353,589-139,355,400
(*) = 1,812bp
Clipping = Left 1,593 soft Read name = derived
Read length = 3,405bp
Reference span = chr22:46,850,466-46,852,049
(*) = 1,584bp
Clipping = Right 1,821 hard Breakpoint amplification system - design

Custom breakpoint amplification

Derivative chr 22
22F/8R

Derivative chr 8
8F/22R

Normal chr 8
8E/8R

Normal chr 22
22E/22R 1.5% TAE Gel image from specific breakpoint PCR amplification

METHOD FOR PREIMPLANTATION GENETIC SCREENING OF EMBRYOS FOR DETECTION OF STRUCTURAL REARRANGEMENTS

CROSS REFERENCE TO RELATED APPLICATIONS

None.

FIELD

The present disclosure relates generally to a method for preimplantation testing of embryos to determine and reduce transmission of balanced chromosomal rearrangements (BCRs).

BACKGROUND

Carriers of balanced chromosomal rearrangements (BCRs) are at risk for infertility, recurrent miscarriages, and abnormal offspring because of unbalanced rearrangements or translocation. A small subgroup of carriers is at risk for neurodevelopmental or neuropsychiatric conditions (Halgren et al., 2018).

Preimplantation genetic testing for structural rearrangements (PGT-SR) allows for the preselection of embryos without chromosomal gains or losses (Munne et al., 2000). However, next-generation, low-pass, whole-genome sequencing, which is the current standard for preimplantation aneuploidy (PGT-A) screening of cells from an embryo biopsy, cannot distinguish between an embryo that carries a BCR and one that does not. Thus, such technology cannot provide information to prospective parents to enable prevention of vertical transmission of the BCR to future generations, nor can such technology detect cryptic potential disease-causing imbalances, complex rearrangements, or gene disruptions at breakpoint sites.

Indirect approaches to genetic-linkage analysis used in PGT-SR, such as single-nucleotide polymorphism (SNP) array or sequencing-based haplotyping, are labor intensive, costly, and limited to familial cases of BCRs because DNA from family members who are known BCR carriers or from embryos with chromosomal unbalances resulting from BCR is required to enable haplotype phasing (Vermeesch et al., 2016). In addition, such approaches cannot detect potential disease-causing cryptic micro-deletions or micro-duplications.

Another technique, mate-pair next-generation sequencing which is also labor intensive, can delineate chromosomal structural rearrangements with abnormal phenotypes but may not perform well when the breakpoint is in a highly repetitive genomic region (Aristidou et al., 2017).

A preimplantation genetic test to discriminate embryos that carry a BCR from those that do not, as well as for detecting cryptic imbalances and/or complex rearrangements, is desirable. Embryos so assessed will have an increased likelihood of success in reproductive technologies.

SUMMARY

It has been found that that a method that permits determination of an embryo's carrier status for a balanced chromosomal rearrangement (BCR) prior to implantation can help prevent vertical transmission of a BCR to the offspring of a BCR carrier parent.

There is described herein a method for determining carrier status of an embryo for a balanced chromosomal rearrangement (BCR) prior to implantation of the embryo, said method comprising: obtaining cells/trophectoderm biopsy (3-10 trophectoderm cells) from the embryo from at least day 4 post in vitro fertilization; conducting long-read nanopore sequencing of the DNA of the parent, carrier of BCR, and of the cells from the embryo; and conducting long-read sequencing data analysis to detect at least one breakpoint; preparing customized primers specific to the breakpoint; employing the customized primers in a polymerase chain reaction customized to the breakpoint (cBP-PCR) to determine whether the breakpoint is indicative of BCR; determining on the basis of cBP-PCR whether the embryo status is BCR carrier or BCR noncarrier; and determining, on the basis of Sanger sequencing, whether the BCR carrier embryo is fully balanced down to single base resolution.

The method may be used for conducting pre-implantation genetic screening of embryos.

Other aspects and features of the present disclosure will become apparent to those ordinarily skilled in the art upon review of the following description of specific embodiments in conjunction with the accompanying figures.

BRIEF DESCRIPTION OF THE FIGURES

Embodiments of the present disclosure will now be described, by way of example only, with reference to the Figures.

DETAILED DESCRIPTION

Figure 1:
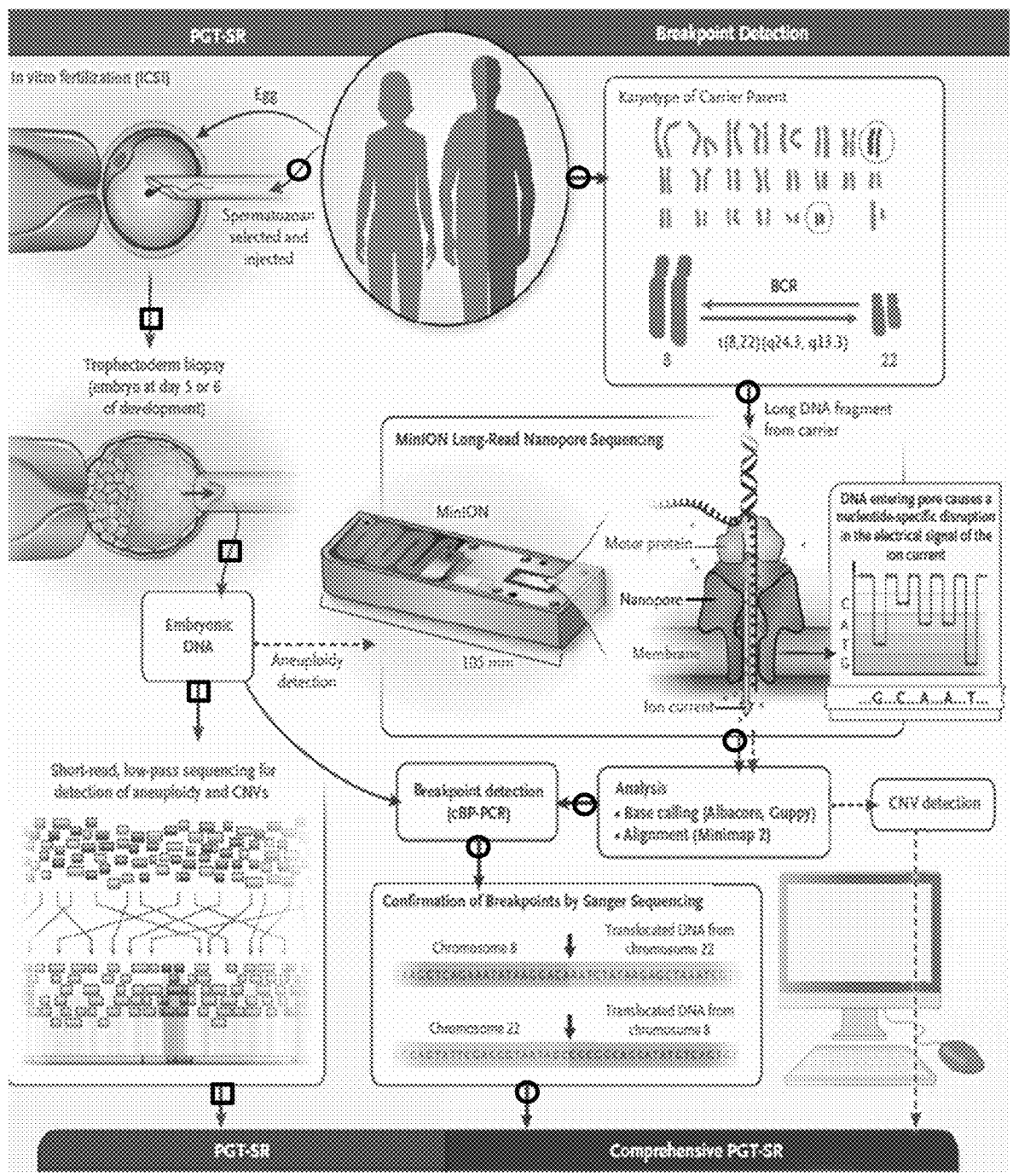
FIG. 1 depicts a schematic methodology for preimplantation genetic testing for structural rearrangements (PGT-SR) with a comprehensive test employing the use of long-read nanopore sequencing with breakpoint confirmation to differentiate embryos for use in reproductive technologies.

The method described herein permits reproductive technologies that prevent vertical transmission of a balanced chromosomal rearrangement (BCR) to the offspring of a BCR carrier.

There is provided herein a method of determining carrier status of an embryo for a balanced chromosomal rearrangement (BCR) prior to implantation of the embryo, the method comprising: obtaining cells/trophectoderm biopsy (3-10 trophectoderm cells) from the embryo from at least day 4 post in vitro fertilization; conducting long-read nanopore sequencing of the DNA of the parent, carrier of BCR, and of the embryo cells, and conducting long-read sequencing data analysis to detect at least one breakpoint; preparing customized primers specific to the breakpoint; employing the customized primers in a polymerase chain reaction customized to the breakpoint (cBP-PCR) to determine whether the breakpoint is indicative of BCR; determining on the basis of cBP-PCR whether the embryo status is BCR carrier or BCR noncarrier; and determining on the basis of Sanger sequencing whether a BCR carrier embryo is fully balanced down to single base resolution.

The method may advantageously be employed when at least one parent of the embryo is a BCR carrier. For example, such a carrier parent may possess a reciprocal translocation, Robertsonian tanslocation, a pericentric inversion, or paracentric inversion.

The cells of the embryo to be assessed may be obtained from the embryo later than day 4 post in vitro fertilization, for example at day 5 or 6 post in vitro fertilization.

The average length of sequenced DNA fragments in the long-read nanopore sequencing may be from about 5 to 15 kb, for example from about 8 to 10 kb. Lengthy or "ultra-long" sequences may be included in the sequencing, for example greater than 50 kb, or greater than 100 kb.

The long-read nanopore sequencing is conducted using a MINION™ sequencer or a GRIDION™ high throughput sequencer (Oxford Nanopore Technologies, Oxford UK). A typical period of time for long-read nanopore sequencing may be, for example, 48 hours.

In the described method, a chromosomal copy-number variation (CNV) plot may be generated from the long-read nanopore sequencing.

In the described method, multiple breakpoints can be detected, and customized primers can be prepared for one, multiple or all breakpoints. Sanger sequencing is conducted to confirm the at least one breakpoint, and full balance can be detected at single base resolution.

Once the embryo is determined to have BCR noncarrier status, the embryo may be implanted into a human subject. Optionally, the embryo may be frozen if BCR noncarrier status is indicated, so as to be ready for later use. Once frozen, such an embryo can be properly stored and later thawed for implanting into a human subject at the desired time.

The preimplantation testing described herein, permits the parents to determine which embryo to select in order to avoid vertical transmission of a BCR to offspring.

Advantageously, the method describes permits accurate discrimination between embryos that carry a balanced chromosomal rearrangement (BCR) and embryos that do not. Advantageously, the determination can be made even when the breakpoint site is in a highly repetitive genomic region. The presence of cryptic imbalances and/or of complex rearrangements may be determined using the described method.

To gain a better understanding of the invention described herein, the following example is set forth, based on multiple embryos from multiple couples pursuing a pregnancy through a reproductive technology. It should be understood that these examples are for illustrative purposes only. Therefore, they should not limit the scope of this invention in anyway.

Example 1

Comprehensive Test for Preimplantation Detection of Translocations in Human Embryos Summary A brief summary of this Example is presented below, followed by detailed background information, methods and results.

This Example involves the direct sequencing of long and ultra-long DNA strands (between tens and hundreds of thousands of kilobases) in real time, with minimal capital cost and user time, on a small hand-held platform (Cretu Stancu et al., 2017). Using this technology, the results of a karyotype-guided PGT-SR protocol was clinically validated by means of low-coverage, long-read sequencing to identify breakpoints, which were manually reviewed and then validated by means of polymerase chain reaction and Sanger sequencing.

Briefly, eleven couples, with one partner who was a BCR carrier, underwent in vitro fertilization at the CReATe Fertility Centre in Toronto between 2016 and 2018. Of the 11 couples, 9 underwent in vitro fertilization with the use of PGT-SR because of a known BCR (seven reciprocal translocations, one pericentric inversion, and one paracentric inversion), and the other 2 couples involved patients in whom a balanced translocation was incidentally discovered after aberrations indicative of a BCR were detected on routine PGT-A analysis. A MINION™ sequencer was used to identify the precise breakpoints in all of the 11 BCR carriers.

Biopsy of the trophectoderm (four to six cells) was performed on 82 blastocysts from these 11 couples, followed by whole-genome amplification with the use of the SUREPLEX™ DNA Amplification System (Illumina) or the REPLI-G™ amplification kit (Qiagen) on the trophectoderm DNA. Standard PGT-SR was performed on all the cell samples from the embryos by means of short-read next-generation sequencing-based testing with the VERISEQ™ PGS (preimplantation genetic screening) kit and the Karyomapping SNP array (Illumina). Of the 82 blastocysts, 27 (33%) were euploid and the rest 55 (67%) were aneuploid or unbalanced.

Using a comprehensive approach of PGT-SR with a MINION™ sequencer, it was found that 11 of the 27 euploid embryos (41%) carried a BCR; the remainder (16 [59%]) tested negative. The comprehensive approach was thus able to distinguish BCR carriers from noncarriers and map the breakpoints with single-base resolution in the embryos that were carriers. These results were confirmed through haplotype phasing and with the genotypes of the six children born to date from this cohort. Concurrent aneuploidy detection is also possible with the use of the MINION™ sequencer and the results from eight representative cases are presented herein below.

The results presented in this example show that a clinical application of long-read nanopore sequencing for preimplantation testing can distinguish embryos that carry a BCR from those that do not and thus can serve in the prevention of vertical transmission of BCRs to the offspring of BCR carriers.

Background

Carriers of balanced chromosomal rearrangements (BCRs) are at risk for infertility, recurrent miscarriages, and abnormal offspring because of unbalanced rearrangements. A small subgroup of carriers is at risk for neurodevelopmental or neuropsychiatric conditions (Halgren et al., 2018). Preimplantation genetic testing for structural rearrangements (PGT-SR) allows for the preselection of embryos without chromosomal gains or losses (Munne et al., 2000). However, next-generation, low-pass, whole-genome sequencing, which is the current standard for preimplantation aneuploidy (PGT-A) screening of cells from an embryo biopsy, cannot distinguish between an embryo that carries a BCR and one that does not and thus does not provide information to the prospective parents that would enable the prevention of vertical transmission of the BCR to future generations and the detection of cryptic potential disease-causing imbalances, complex rearrangements, or gene disruptions at breakpoint sites. Indirect approaches to genetic-linkage analysis used in PGT-SR, such as single-nucleotide polymorphism (SNP) array or sequencing-based haplotyping, are labor intensive, costly, and limited to familial cases of BCRs because DNA from family members who are known BCR carriers or from embryos with chromosomal unbalances resulting from BCR is required to enable haplotype phasing (Vermeesch et al., 2016). In addition, such approaches cannot detect potential disease-causing cryptic micro-deletions or microduplications (Vermeesch et al., 2016).

The technique of mate-pair next-generation sequencing is also labor intensive, and while it can delineate chromosomal structural rearrangements with abnormal phenotypes, it may not perform well when the breakpoint is in a highly repetitive genomic region (Aristidou et al., 2017).

This example illustrates that embryos can be accurately distinguished to show which embryos carry a BCR and which embryos do not. Further, it is possible to detect the presence of cryptic imbalances and complex rearrangements, using PGT-SR with the MINION™ long-read nanopore sequencer (Oxford Nanopore Technologies).

Methods & Results

Patient Samples

This study was approved by the University of Toronto Research Ethics Board (REB no. 30251) and informed consent was obtained from all participants. Eleven couples, with one of the partners being a carrier of a balanced chromosomal rearrangement (BCR), underwent IVF at the CReATe Fertility Centre, Toronto, Canada from 2016-18. Nine were undergoing IVF with PGT-SR due to known BCR (7 reciprocal translocations, 1 pericentric inversion, 1 paracentric inversion), and 2 were referred for IVF-PGT-A testing where the male was diagnosed with a balanced translocation after detection of BCR indicative chromosomal aberrations in their embryos. Ten couples completed one IVF cycle after recruitment and had all blastocysts biopsied for PGT-SR. Two couples completed more than one IVF cycle and WGA DNA was batched from all of their embryos and tested together.

Confirmatory postnatal testing on 5 children born to date was performed. From each couple and/or affected family member whole blood collected with EDTA was used for DNA extraction while from patient carrier of BCR peripheral blood mononuclear cells were collected for evaluation of allele drop out (ADO) frequency for the established cBP-PCR in WGA samples.

Embryonic DNA Samples

Embryos were created through in vitro fertilization (IVF) of mature (metaphase II) oocytes by intracytoplasmic sperm injection (ICSI). After ICSI, the fertilized oocytes were cultured individually from Day 1 (D1) to D5/6 in Sage 1-Step medium with serum protein supplement (Origio, Canada) under oil, in 25-µL droplets. Trophectoderm (TE) biopsy of 4-6 cells was performed on a total of 82 blastocysts from the 11 couples using laser-assistance performed in Global "total" w/Hepes and protein medium (LifeGlobal, Canada) under oil. All embryos were cryopreserved by vitrification after laser collapse of the blastocoel cavity, as per standard procedures (Darwish et al., 2016).

WGA using the SUREPLEX™ system (Illumina, CA) or the REPLI-G™ kit (QIAGen, Germany) using the manufacturer's protocols, was performed on the TE biopsy cells. Embryonic WGA DNA was quantified by QUBIT™ instrumentation and examined for size distribution on a 1% e-Gel.

Standard PGT-SR short read NGS based testing was performed using the VERISEQ™ PGS kit (Illumina, CA).

Study Design

A workflow for comprehensive PGT-SR to distinguish embryos carrying a BCR from non-carriers at single-base resolution was developed and clinically validated with the MINION™ sequencer (long read sequencing) (Oxford Nanopore Technologies ONT, UK) that streamlined implementation within the current clinical PGT-SR (short read sequencing) diagnostic processes. The target timeline to result delivery from the comprehensive PGT-SR testing was within 7 days of embryo biopsy.

FIG. 1 provides a schematic representation of preimplantation genetic testing for structural rearrangements with the use of Long-Read Nanopore Sequencing, as described herein. Arrows marked with a circle indicate the approach used for the delineation of balanced translocations and inversions after long-read DNA sequencing is performed with the MINION™ nanopore sequencer (Oxford Nanopore Technologies). Such delineation allows for breakpoint confirmation by means of a polymerase-chain-reaction (PCR) assay customized to the breakpoint (cBP-PCR), together with single-base resolution of the breakpoint by means of Sanger sequencing. High-molecular-weight DNA extracted from balanced chromosomal rearrangement (BCR) carriers was fragmented, and libraries were prepared for long-read sequencing with the use of the SQK-LSK108 ligation kit (Oxford Nanopore Technologies). Long-read sequencing was performed on the MINION™ sequencer over 48 hours.

The average length of the sequenced fragments was approximately 8 to 10 kb, with the longest reads reaching over 100 kb. Karyotype-guided computational analysis identified derivative reads and mapped breakpoints. The use of custom-designed PCR primers and Sanger sequencing yielded confirmation of breakpoints within 7 days after the sample was submitted.

The arrows marked with a square indicate the approach used for preimplantation testing for structural rearrangements (PGT-SR) with short-read sequencing, which can detect only chromosomal gains and losses (and not BCRs) in embryos. Cells from in vitro fertilized embryos of couples undergoing PGT-SR were biopsied on day 5 or 6 of development (before vitrification) to obtain DNA for aneuploidy (chromosomal copy-number variation [CNV]) detection and for the discrimination of embryos that do not carry a BCR from those that do with the use of the custom breakpoint PCR designed for the BCR-carrier parent.

The dashed arrows indicate an approach in which embryonic DNA obtained from the same trophectoderm biopsy sample can also be used for aneuploidy detection by means of sequencing with the MINION™ sequencer and an algorithm for CNV analysis. ICSI denotes intracytoplasmic sperm injection.

Figure 2:
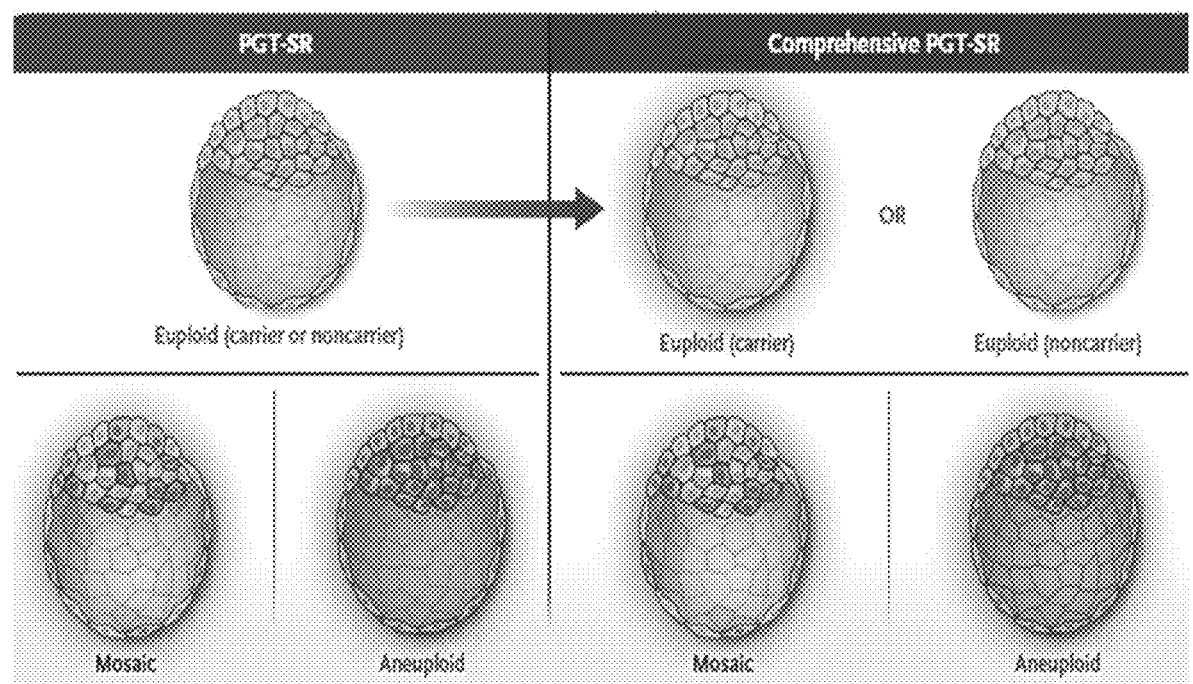
FIG. 2 shows that comprehensive methodology depicted in FIG. 1 can differentiate euploid embryos as carrier versus noncarrier.

FIG. 2 shows a schematic of the evaluation of embryos from FIG. 1 in regard to preimplantation genetic testing for structural rearrangements (PGT-SR) when comprehensive PGT-SR, is used to differentiate with regard to Euploid (carrier), Euploid (noncarrier), mosaic and aneuploid embryos.

Localization and determination of orientation of the two chromosomal breakpoints was conducted using low coverage sequencing of the carrier partner with the MINION™ sequencer and analysis guided by the karyotype (determined by previous cytogenetic testing). With this information custom PCR primers were designed to allow for breakpoint amplification and confirmation using Sanger sequencing. Next, this custom designed breakpoint PCR (cBP-PCR) was used for pre-implantation testing on whole genome amplified (WGA) DNA from embryos. After amplification, Sanger sequencing achieved single base resolution of the rearrangement. Aneuploidy testing (PGT-A) on WGA DNA from embryos was performed with standard PGT-A VERISEQ™ NGS technology (Illumina, CA) on a MISEQ™ system (Illumina, CA). Copy number analysis for aneuploidy testing was also performed using DNA ligation kit on a MINION™ sequencer. SNP array Karyomapping (Illumina, CA) was also used to confirm findings from data generated using the MINION™ sequencer in the cases where DNA from an affected child or embryo with an unbalanced chromosomal rearrangement was available for haplotyping (Wang et al, 2017; Handyside et al., 2010).

Table 1 provides information illustrating that balanced structural rearrangements (BCR) in patients and their IVF created embryos undergoing comprehensive PGT-SR to distinguish euploid BCR-carrier from non-carrier embryos. Parental karyotype guided analysis of nanopore sequencing data from the MINION™ sequencer determined the genomic location of the breakpoint utilized to diagnose embryos BCR carriers.

TABLE 1

Balanced structural rearrangements (BCR) in patients and their IVF created embryos

| Case | Chromosomal rearrangement (Karyotype) | Nanopore Breakpoint Detection (Hg38) (Orientation) | Total biopsied blastocysts | Unbalanced/ aneuploid embryos | Euploid/ BCR carriers[$] | Euploid[#] | BCR carriers[#] |
|---|---|---|---|---|---|---|---|
| TC-1 | 46, XX, t(8; 22) (q24.3; q11.2) | chr8: 139353588 (+); chr22: 46852062 (+) | 4 | 1 | 3 | 2 | 1 |
| TC-2 | 46, XX, t(1, 2) (p34.1; p13) | chr1: 46843185 (+); chr2: 71426279 (+) | 14* | 11 | 3 | 1 | 2 |
| TC-3 | 46, XX, t(6, 14) (p25; q23.3) | chr6: 3042566 (+); chr14: 64741771 (−) | 5 | 2 | 3 | 2 | 1 |
| TC-4 | 46, XY, inv(4) (p16.3; q32.3) | Chr4p16.3: 49256596 (−); chr4q32.2: 160864117(+) | 4 | 2 | 2 | 0 | 2 |

TABLE 1-continued

Balanced structural rearrangements (BCR) in patients and their IVF created embryos

| Case | Chromosomal rearrangement (Karyotype) | Nanopore Breakpoint Detection (Hg38) (Orientation) | Total biopsied blastocysts | Unbalanced/ aneuploid embryos | Euploid/ BCR carriers$ | Euploid# | BCR carriers# |
|---|---|---|---|---|---|---|---|
| TC-5 | 46, XX, t(1:22) (p36.2; q13.3) | chr1: 7789560 (+); chr22: 48969135 (−) | | | | | |
| TC-6 | 46, XX, inv (8) (q13; q24.3) | chr8q13: 69999154(+); chr8q24.3: 142849210(−) | 3 | 1 | 2 | 1 | 1 |
| TC-7 | 46, XX, t(11: 22) (q23.2; q11.2) | chr11: 116812508(+); chr22: 20339429(+) | 3 | 3 | 0 | 0 | 0 |
| TC-8 | 46, XX, t(11: 12) (11q24.2; q12q14.3) | chr11: 124203274(+); chr12: 67201427 (+) | 25** | 19 | 6 | 3 | 3 |
| TC-9^ | 46, XY, t(8: 11) (q24.13, q23.3) | chr8: 124483128(+); chr11: 116814391(+) | 6 | 4 | 2 | 1 | 1 |
| TC-10 | 46, XY, t(8; 12) (q24.22; q14) | chr8: 137676929(+); chr12: 73058076(+) | 5 | 2 | 3 | 1 | 2 |
| TC-11^ | 46, XY, t(1; 6) (p32.2; p22.3) | chr1: 57376472(+); chr6: 16984092(+) | 13 | 10 | 3 | 1 | 2 |

$Standard short read sequencing PGT-SR utilizes low pass (0.1x coverage, short read) whole genome sequencing and has inherent limitation to distinguish euploid embryos BCR carriers from non-carriers
Nanopore long read sequencing PGT-SR enables discrimination of euploid BCR carriers from non-carriers embryos by accurate delineation of the chromosomal rearrangement in parents BCR carriers
*Embryos from 3 IVF cycles (3OPU);
**Embryos from 5 IVF cycles (5OPU)
^Incidental finding of balanced translocation in the parent. Preimplantation testing of their embryos revealed high rate of unbalanced aberrations indicative for BCR carriers. The MINION ™ nanopore sequencer determined the breakpoints that were independently confirmed by karyotype and FISH analysis of the parent.

Figure 3:
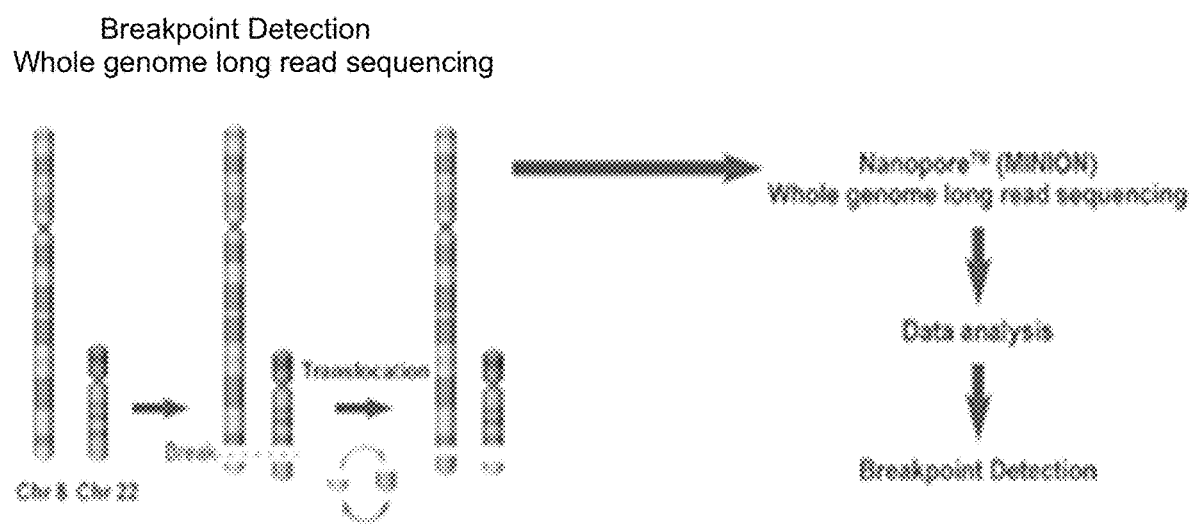
FIG. 3 depicts a schematic of breakpoint detection using a nanopore MINION™ sequencer. Breakpoints in the parent, TC-1 and affected child were found on both chromosomes. Breakpoint locations were consistent with the karyotyping coordinates but were ~500 kb and ~2 Mb upstream from the breakpoints identified for chr 8 and for chr 22 with SNP array, respectively.
Figure 4:
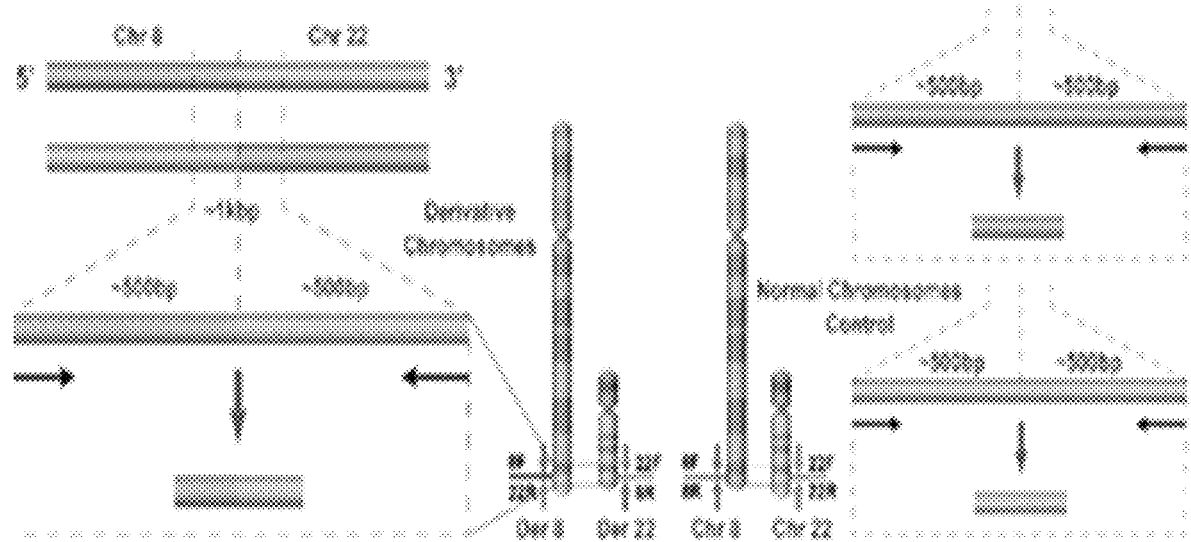
FIG. 4 depicts a schematic of custom primer design, based on breakpoints and corresponding normal chromosomes, for amplification was via PCR (cBP-PCR).

FIG. 3 and FIG. 4 represent the establishment of nanopore sequencing strategy for detection of breakpoints in BCR carriers. In FIG. 3, using the nanopore MINION™ sequencer the breakpoints were determined in the parent, TC-1 (46,XX,t(8:22)(q24.3,q13.33), and affected child (22q13 deletion syndrome, [arr[hg19]: 8q24.3 (140,366, 315-146,295,771)x3, 22q13.31q13.33 (47,254,703-51,176, 099)x1]) on both chromosomes at ~4× genome coverage, producing 5 reads (6 kb±560 bp) spanning the breakpoints of derivative chromosomes. The breakpoint locations were consistent with the karyotyping coordinates but were ~500 kb and ~2 Mb upstream from the breakpoints identified for chr8 and for chr 22 with SNP array, respectively. The breakpoints and corresponding normal chromosomes were amplified (using custom primers cBP-PCR), as schematically represented in FIG. 4.

Sanger sequencing was used to identify the breakpoint location to a single base resolution. Single base resolution (a breakpoint for balanced carrier) is located: Chr 8-139353389-139353718 (breakpoint 139,353,588), and Chr 22-46851362-46852103 (breakpoint 46,852,062). The primers were validated and tested for robustness against the balanced carrier (TC-1), affected child (TC-1_P), non-carrier DNA (TC-1_1-father) and on low template WGA (a sample of 5 single lymphocytes from the mother) (TC-1_SC), correctly determining the carrier status.

Figure 5:
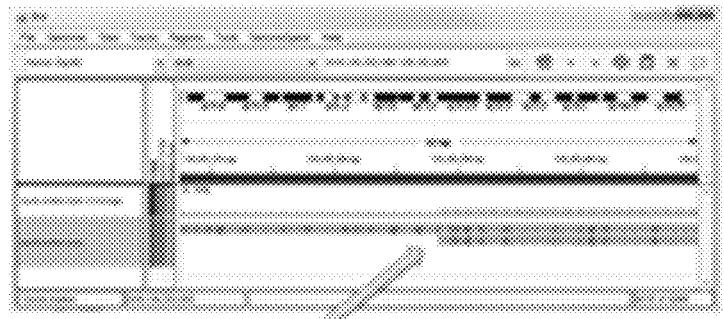
FIG. 5 depicts screen shots of the analysis conducted for chr 8 (upper) and chr 22 (lower).
Figure 5:
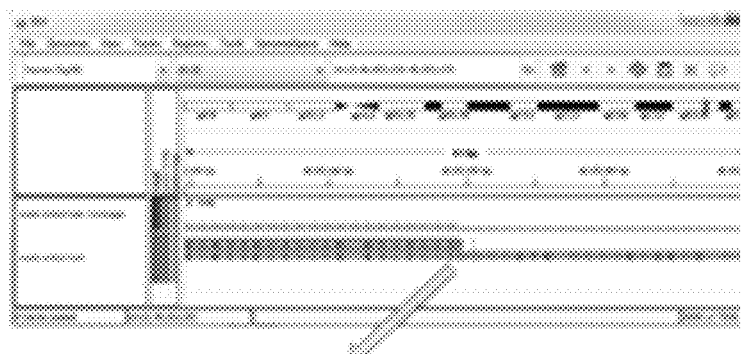

FIG. 5 provides computer screen shots of data pertaining to FIG. 3 and FIG. 4 with regard to Chr 8 (upper panel) and Chr 22 (lower panel), respectively:

Read name=derived, Read length=3,405 bp, Reference span=chr8:139,353,589-139,355,400, (+)=1,812 pb, Clipping=Left 1,593 soft; and Read name=derived, Read length=3,405 bp, Reference span=chr22:46,850,466-46,852,049, (+)=1,584 pb, Clipping Right 1,821 hard.

Figure 6:
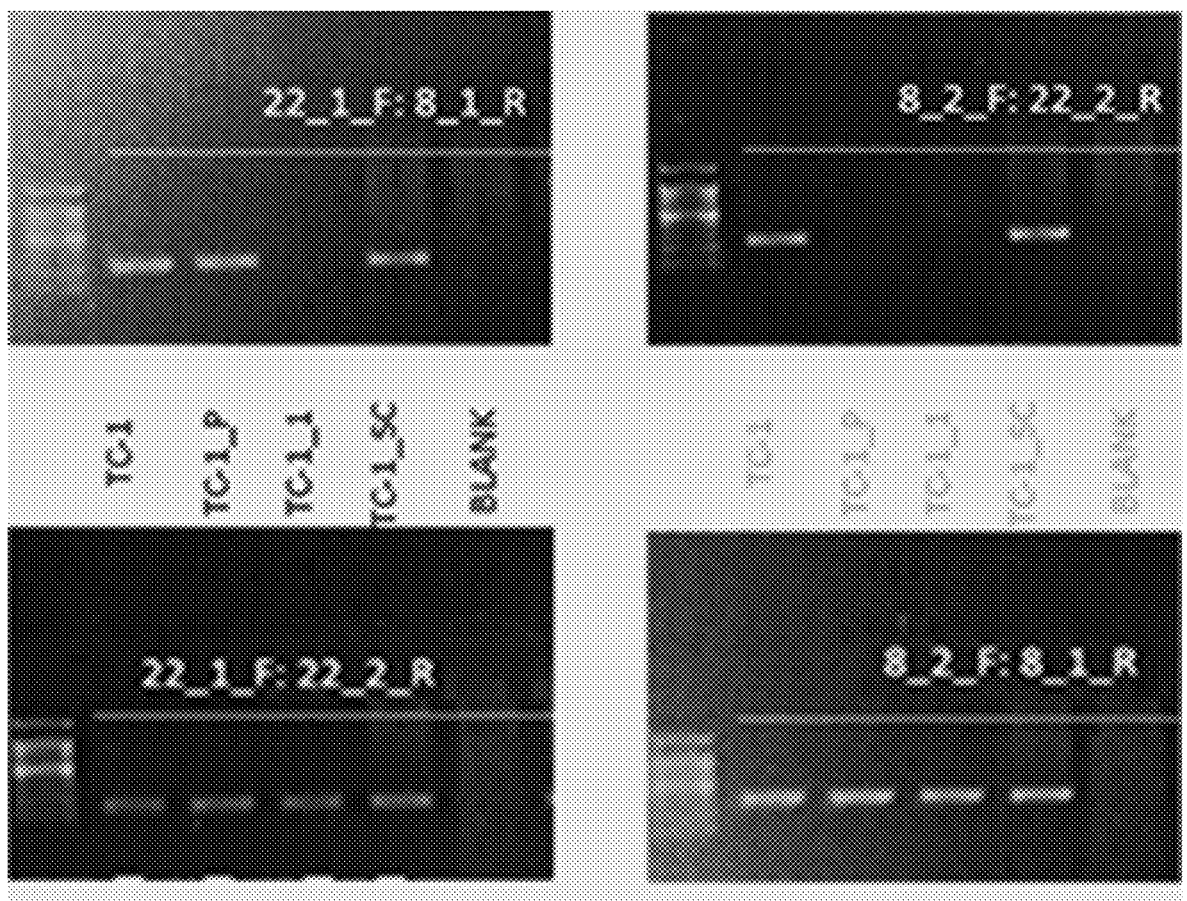
FIG. 6 depicts a chromatographic separation for validation based on the balanced carrier (TC-1); affected child (TC-1_P); non-carrier DNA (TC-1_1-father); and on low template WGA based on a sample of 5 single lymphocytes from the mother (TC-1_SC), thus validating a correct determination of carrier status.

FIG. 6 S1R-L illustrates chromatographic evaluation pertaining to 22_1_F:8_1_R and 8_2_F:22_2_R for the upper panels, respectively; and 22_1_F:22_2_R and 8_2_F:8_1_R for the lower panels, respectively.

Long Read Nanopore Sequencing with MINION™ Sequencer.

Genomic DNA was extracted from peripheral blood from each partner and affected or unaffected children (if available) following a modified Phenol/Chloroform protocol to obtain high molecular weight DNA (hmwDNA) from 4 mL (EDTA) peripheral blood. Briefly after red cell lysis (1×Pharm lyse buffer, DB Biosciences), white blood cells were lysed in Proteinase K/SDS (0.5c/ow/v) TRIS-HCl buffer; and protein precipitation and DNA extraction were performed using standard Phenol/Phenol-Chlorophorm-Iso-amylalchohol DNA extraction protocols. The quality and integrity of the DNA was measured by NANODROP™ spectrophotometer and QUIBIT™ 2.0 fluorometer (Life Sciences).

1 μg of hmwDNA was sheared to ~10-20 kb fragments using G-tubes (Covaris). Genomic libraries were prepared using the Oxford Nanopore 1D-ligation library prep kit SQK-LSK108 following ONT protocol (Oxford Nanopore Technologies, UK). A 0.4× (instead of 1×) AMPure magnetic beads (Beckman Coulter, A63881) clean-up was introduced after the end-repair steps (NEBNext Ultra II end-repair/dA-tailing module (New England BioLabs; E7546)) in the protocol to remove small DNA fragments. For 1D library the ligation reaction was prepared as follows: 30 µL of water (DNA), 20 µL of adaptor mix and 50 µL of blunt/TA ligase master mix (New England BioLabs; M0367).

Ligation was carried out at room temperature for 15 min. The AMPure XP beads were re-suspended at room temperature by vortexing. 40 µL of beads were added into the ligation product. The beads were washed twice with 140 µL of adaptor bead binding buffer and eluted in 25 µL of elution buffer. The eluted product was the adaptor-ligated library that was prepared for sequencing using the pre-sequencing mix and loading beads used in nanopore sequencing. Each genomic library was loaded and sequenced on a R9.4 flowcell supported by MinKNOW™ software v 2.13 (ONT) for 48 hours on a MINION™ sequencer using MinKNOW™ software v 2.13 (ONT). The total technician hands-on time for library preparation was 30 min with 2 hours overall time.

Nanopore Sequencing Data Analysis for Detection of Breakpoints.

An analytical pipeline was developed for breakpoint detection which involves base calling, alignment, data quality filtering, local search and extraction of reads aligning to candidate BCR regions determined by karyotyping in all patients, followed by visual inspection. Basecalls were generated from the MINION™ sequencer data using Albacore™ (version 2.2.7). Reads passing the basecaller's quality filter (mean quality score ≥7) were aligned to the hg38 human reference with minimap2, version 2.1-r311 (Li, 2018). Each sample's run-level alignments were merged into a single per sample alignment (BAM format) using samtool[6] (Li, 2009). For suspected genomic rearrangements, karyotype coordinates were converted to genomic coordinates using the UCSC hg38 genome build, and reads that aligned to both of the regions were extracted. A local search was done for supporting reads in the aligned MINION™ sequencer data followed by visual inspection with the IGV genome browser. This analysis pipeline allowed confirmation of breakpoints for abnormalities previously discovered through cytogenetics with a mean genome coverage of 3.5×, and an average read length of 4 kb (see Table 2).

After identification of the breakpoint junctions and orientation of the rearranged fragments, flanking DNA sequences 500 bp upstream from the breakpoints were extracted to create a cBP-PCR system enabling amplification over each breakpoint's flanking region and the respective regions of the two normal chromosomes (Untergasser et al., 2012). All cBP-PCR products from parental DNA and embryo WGA DNA samples were also analyzed by Sanger sequencing (3500 Genetic Analyzer, Applied Biosystems) using BigDye™ v3.1 to confirm the breakpoint and non-breakpoint flanking sequences and provide single-base resolution of the breakpoint.

Table 2 shows long-read nanopore sequencing metrics presenting the yield, quality of sequencing and diagnostic yield of split reads per patient. Raw coverage is calculated from sequencing yield and a genome size of 3.3 Gb.

TABLE 2

| | Long-read nanopore sequencing metrics | | | | | |
|---|---|---|---|---|---|---|
| Sample | No of Flowcells | Number of reads | Number of bases (GB) | Average read length (Bp) | Raw Coverage (X) | Number of putative breakpoint reads |
| TC-1 | 4 | 967,849 | 10.6 | 10952.12 | 3.21 | 5 |
| TC-2 | 3 | 885,617 | 9.1 | 10275.32 | 2.76 | 6 |
| TC-3 | 6 | 2,393,639 | 21.3 | 8898.58 | 6.45 | 4 |
| TC-4 | 4 | 1,165,964 | 13.5 | 11578.40 | 4.09 | 2 |
| TC-5 | 3 | 934,209 | 10.1 | 10811.29 | 3.06 | 3 |
| TC-6 | 1 | 823,265 | 6.69 | 8126.18 | 2.03 | 6 |
| TC-7 | 2 | 1,803,316 | 13.17 | 7303.21 | 3.99 | 2 |
| TC-8 | 2 | 1,416,138 | 12.17 | 8593.80 | 3.69 | 3 |
| TC-9 | 7 | 6,245,003 | 16.65 | 2665.73 | 5.05 | 2 |
| TC-10 | 2 | 3,232,042 | 23.91 | 7397.80 | 7.25 | 6 |
| TC-11 | 1 | 3,686,153 | 16.43 | 4457.75 | 4.98 | 4 |

Nanopore Library Preparation and Sequencing of Embryonic WGA DNA.

Whole genome sequencing (WGS) using the MINION™ sequencer was performed on 6 WGA embryonic DNA samples. 1 µg of WGA DNA was first repaired using T7-exonuclease (New England BioLabs, UK) to remove DNA branching, then sheared using G-tubes (Covaris). The same 1D-ligation library preparation kit (SQK-LSK108) described above was used as for genomic DNA. Libraries from each embryo were loaded and sequenced on a R9.4 flowcell supported by MinKnow™ software v 2.13 (ONT) for 48 hours on MinION the MINION™ sequencer. Additionally, we developed an analytical pipeline to detect copy number variations in WGA DNA from embryos and provide PGT-A result based on nanopore sequencing.

Detection of Copy Number Variants (CNV) in Embryo WGA Using Nanopore Sequencing.

Bias in WGA leads to the artificial inflation of read counts and poses a challenge to analyse copy number variations (CNV). An open-source tool Ginkgo™, was used to address these issues and detect CNVs with low coverage sequencing (Garvin et al., 2015). Aligned reads were binned into 1 Mb variable-length intervals across the genome to assess GC bias and coverage dispersion. Cohorts TC-1, TC-2 and TC-3 were used as a reference to normalize bin counts and to eliminate biases uncorrected by GC normalization (Wei et al., 2018). Copy-number profiles of individual biopsies were constructed with a better signal-to-noise ratios, and was reliable for accurate copy-number calls.

Figure 7:
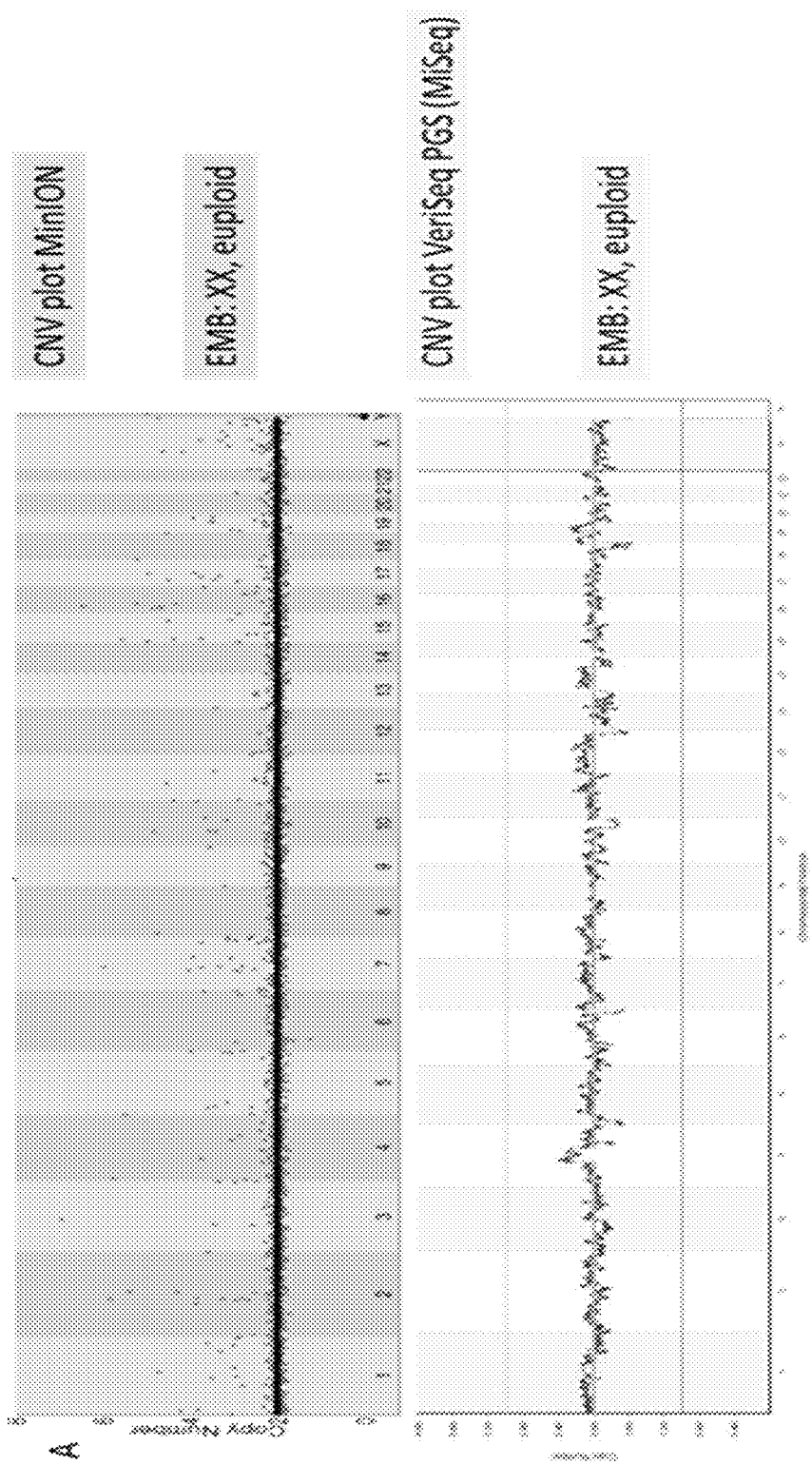
FIG. 7 depicts a CNV plot generated using whole genome sequencing data from a MINION™ sequencer compared to standard short read sequencing for a euploid, XX embryo (EMB-2, TC-1).
Figure 8:
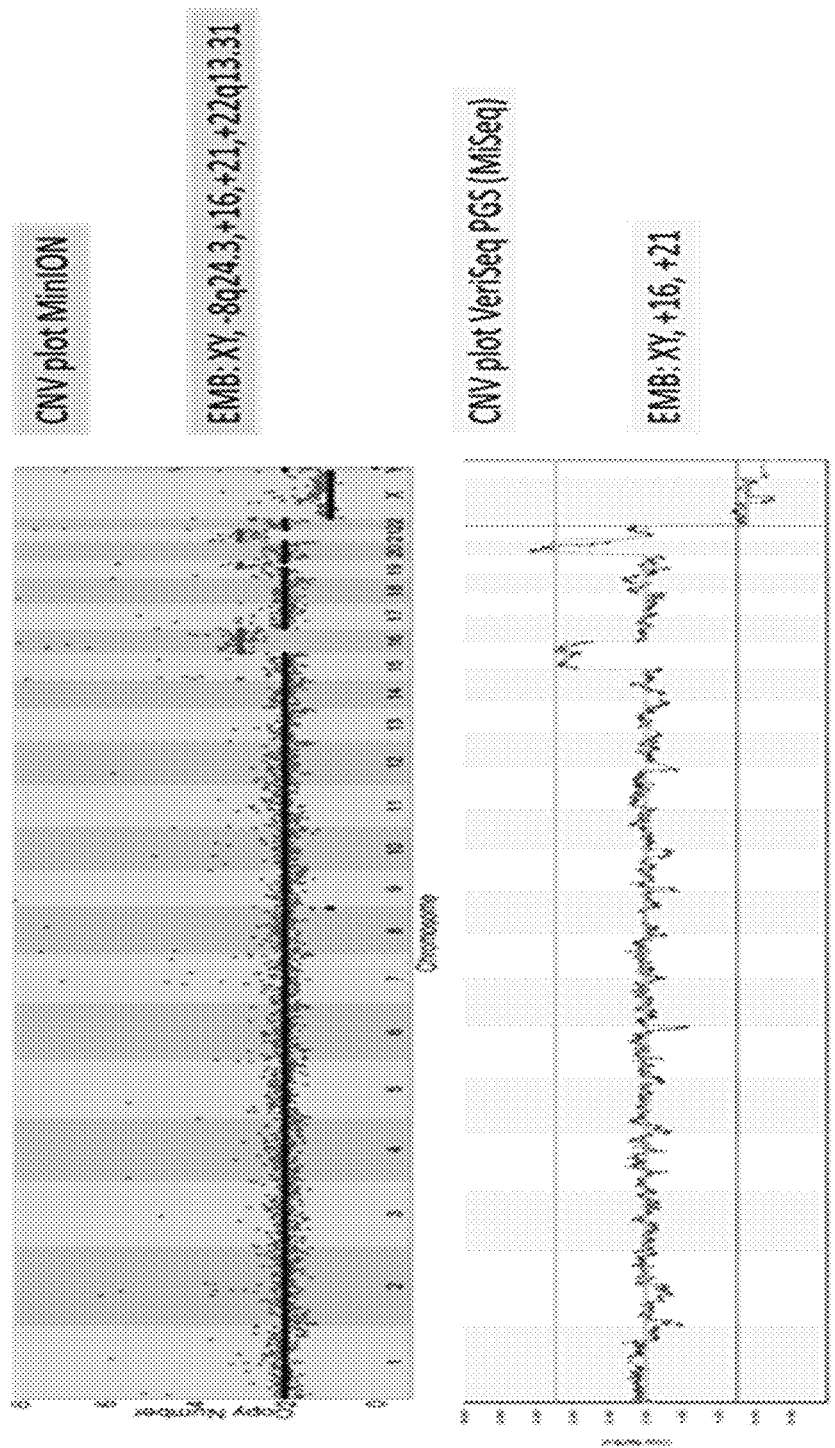
FIG. 8 depicts a CNV plot generated using whole genome sequencing data from a MINION™ sequencer compared to standard short read sequencing for an aneuploid, XY embryo with trisomy 16 and 21 and the del/dup associated with unbalanced translocation del8q24.3, dup22q13.31 (EMB-6, TC-1).

FIG. 7 and FIG. 8 show the detection of chromosomal CNV (aneuploidy) in embryos using the MINION™ sequencer. CNV plots generated using the MINION™ sequencer for whole genome sequencing data compared to standard short read sequencing using the VERISEQ™ PGS kit on the MISEQ™ system. The X axis on each plot represents chromosomes 1-22, X and Y; Y axis represents copy number of each region, and gains and losses are indicated by dots. FIG. 7 provides a CNV plot presenting a euploid, XX embryo (EMB-2, TC-1) and FIG. 8 illustrates aneuploidy, XY embryo with trisomy 16 and 21 and in addition it detected the del/dup associated with unbalanced translocation del18q24.3, dup22q13.31 (EMB-6 from patient TC-1).

Table 3 summarizes the concordance between the CNV result of the MINION™ sequencer and the VERISEQ™ PGS kit result. Eight embryos were sequenced with the MINION™ sequencer, as a proof of principle, and CNV detection using the method described above was compared to the clinical PGT-A (VERISEQ™ PGS Kit). The close concordance of the results validates this methodology.

TABLE 3

Long-read nanopore sequencing CNV detection in embryos

| Sample | MINION™ sequencer CNV result | VERISEQ™ PGS kit result |
| --- | --- | --- |
| EMB-2, TC-1 | 46, XX | 46, XX |
| EMB-3, TC-1 | 46, XX | 46, XX |
| EMB-5, TC-1 | 46, XX | 46, XX |
| EMB-6, TC-1 | 48, XY: +16; +21; −8q24.3 (6.9 Mb); +22q13.31 (4.3 Mb) | 48, XY: +16; +21 |
| EMB-4, TC-3 | 46, XY | 46, XY |
| EMB-6, TC-3 | 46, XY | 46, XY |
| EMB-1, TC-4 | 46, XX | 46, XX |
| EMB-1, TC-8 | 45, XX, −16 | 45, XX, −16 |

Design and Validation of Custom Breakpoint Amplification System—cBP-PCR.

Bioinformatics analysis of the MINION™ sequencer data identified candidate breakpoints from reads that mapped to derivative chromosomes from the BCR. The analysis provided the breakpoint location within 100 bp (up or downstream) of the actual breakpoint. After identification of the approximate breakpoint junctions and the orientation of the rearranged fragments, flanking DNA sequences 500 bp upstream were extracted. Primer3 (Untergasser et al., 2012) was used to design PCR primers using these flanking sequences. Candidate primers were screened for off-target amplification using the UCSC Genome Browser's in-silico PCR tool. The candidate diagnostic PCR (cBP-PCR) system consisted of two sets of primers used in four different combinations, allowing for amplification over each breakpoint's flanking region and the respective regions of the two normal chromosomes.

For the affected chromosomes, amplicons were designed either around contacting sequences from the 2 chromosomes involved in the translocation or 2 distant chromosomal regions in cases of inversion. In cases where the translocated strand was in an opposite orientation, 2 additional primer pairs were designed to amplify the normal chromosome in the region corresponding to the one flanking the breakpoints. Primers were tested and validated against 10 ng of carrier and non-carrier parental DNA, as well as 50 ng of WGA DNA from all embryos (see FIG. 3 to FIG. 6).

PCR reactions were carried out in a total volume of 25 µL using QIAGen PCR Master mix and 100 pmol of each primer. Primers were designed to have T, of 60° C. and standard cycling times for fragments between 250-750 bp. All PCR products derived from parental DNA and embryo WGA DNA samples were analyzed by Sanger sequencing (3500 Genetic Analyzer, Applied Biosystems) using BigDye v3.1 to confirm the breakpoint and non-breakpoint flanking sequences and provide breakpoint single base resolution.

Allele Drop Out (ADO) Testing Using Parental Mononuclear Cells.

Peripheral blood mononuclear cells (PBMCs) were collected by gradient centrifugation of 4 mL (EDTA) blood from TC-1 and used for evaluation of allele drop out (ADO) frequency for the established CDB-PCR in WGA samples. In brief, the blood was diluted 4× with phosphate buffered saline (PBS). Subsequently 13 mL of Histopaque®-1077 (family 1; Sigma-Aldrich 10771-500ML) was added per 35 mL of diluted blood. The resulting mixture was centrifuged at room temperature for 20 minutes at 900×g, followed by recovery of the PBMC layer. PBMC were washed twice using PBS, centrifuged at 750×g for 5 minutes, and re-suspended in PBS with 50% DMSO. Low template samples were created by WGA of 5-6 PBMC using SurePlex™ (Illumina, Calif.), following the manufacturer's suggested protocol.

Standard PGT-SR Using Short Read NGS.

Whole genome copy number variation (CNV) analysis was performed by whole genome low pass (0.1×) NGS, using the VeriSeq™ PGS Kit (Illumina, CA). Briefly, after WGA according to manufacturer's instructions, gDNA was tagmented and amplified. The amplified DNA was indexed, purified using AMPure XP beads (1:1 ratio), and normalized with magnetic beads. Normalized libraries were pooled, denatured, and sequenced using a MISEQ™ system (single-end, 1×36 bp). BlueFuse Multi™ Illumina, CA) was used for chromosome CNV analysis and data visualization. The optimal metrics for PGS are 500,000 reads passing filter and a sample noise score (Derivative Log Ratio—DLR) of <0.2; 250,000 reads and DLR <0.4 is clinically acceptable. Reporting resolution is 10 Mb in size for copy number aberrations and >30% for of mosaicism level.

Repeat Analysis

RepeatMasker (www.repeatmasker.org) determined whether the breakpoints fall in regions containing repetitive sequences and, if so, the class of repeats. DNA sequences from split reads spanning the breakpoint were extracted from the nanopore read and annotated to different repeat classes by alignment with public annotated repeat sequences using RepeatMasker. The proximity of the breakpoint to coding/non-coding genes was estimated and is presented in Table 4 for TC-1 to TC-6 and Table 5 for TC-7 to TC-11.

TABLE 4

Summary of repeat elements 1 kb 5' and 3' of the breakpoints determined by sequencing with MINION™ SEQUENCER (TC-1 to TC-6)

| | TC-1 t(8; 22) q24.3; q11.2 | | TC-2 t(1, 2) p34.1; p13 | | TC-3 t(6, 14) p25; q23.3 | | TC-4 Inv (4) p16.3; q32.3 | | TC-5 t(1: 22) p36.2; q13.3 | | TC-6 Inv (8) q13; q24.3 | |
|---|---|---|---|---|---|---|---|---|---|---|---|---|
| Repeat Class | chr 8 | chr 22 | chr 1 | chr 2 | chr 6 | chr 14 | chr 4 | chr 4 | chr 1 | chr 22 | chr 8 | chr 8 |
| DNA | | | | | | | | | | | 1 | |
| LINE | 2 | 1 | 1 | | | 2 | 3 | 3 | 3 | 1 | | 3 |
| LTR | | | | 1 | | 3 | | 3 | 3 | 1 | | |
| SINE | 1 | | 1 | 1 | | 2 | 1 | 1 | 1 | | 4 | 1 |
| Satellite | | | | | | | | | | | | |
| Simple Repeat | | | | | | | | | 1 | | | 1 |
| Repeat Families | chr 8 | chr 22 | chr 1 | chr 2 | chr 6 | chr 14 | chr 4 | chr 4 | chr 1 | chr 22 | chr 8 | chr 8 |
| Alu | 1 | | 1 | 1 | | 2 | 1 | 1 | 1 | | 3 | 1 |
| CR1 | | | | | | | | | | | | |
| ERV1 | | | | | 3 | | | | | | | |
| ERVL | | | | | | | | | | 1 | | |
| ERVL-MaLR | | | 1 | | | | | 3 | 3 | | | |
| L1 | 2 | 1 | 1 | | | 2 | 3 | 3 | 2 | 1 | | 3 |
| L2 | | | | | | | | | | | | |
| MIR | | | | | | | | | 1 | | 1 | |
| Satellite | | | | | | | | | | | | |
| Simple Repeat | | | | | | | | | 1 | | | 1 |
| hAT-Blackjack | | | | | | | | | | | 1 | |
| hAT-Charlie | | | | | | | | | | | | |

TABLE 5

Summary of repeat elements 1 kb 5' and 3' of the breakpoints determined by sequencing with MINION™ SEQUENCER (TC-7 to TC-11)

| | TC-6 Inv (8) q13; q24.3 | | TC-7 t(11: 22) q23.2; q11.2 | | TC-8 t(11: 12) 11q24.2, q12q14.3 | | TC-9 t(8: 11) q24.13, q23.3 | | TC-10 t(8; 12) q24.22; q14 | | TC-11 t(1; 6) p32.2; p22.3 | |
|---|---|---|---|---|---|---|---|---|---|---|---|---|
| Repeat Class | chr 8 | chr 8 | chr 11 | chr 22 | chr 11 | chr 12 | chr 8 | chr 11 | chr 8 | chr 12 | chr 1 | chr 6 |
| DNA | 1 | | | | | | | | 1 | 1 | | |
| LINE | | 3 | 5 | | 3 | 1 | 1 | 2 | 1 | 2 | 4 | 1 |
| LTR | | | | 1 | | | | 1 | 1 | 2 | 2 | 1 |
| SINE | 4 | 1 | 2 | 3 | | 2 | 2 | 2 | | 2 | | |
| Satellite | | | | 1 | | | | | | | | |
| Simple Repeat | | 1 | 1 | 2 | | | 1 | | | | | |
| Repeat Families | chr8 | chr8 | chr11 | chr22 | chr11 | chr12 | chr8 | chr11 | chr8 | chr12 | chr1 | chr6 |
| Alu | 3 | 1 | 2 | 3 | | 1 | 2 | 2 | | 2 | 1 | 1 |
| CR1 | | | 1 | | | 1 | | | | | | |
| ERV1 | | | | | | | | | | | | |
| ERVL | | | | | | | | | | | | |
| ERVL-MaLR | | | 1 | | | | | 1 | 1 | 2 | | |
| L1 | | 3 | 2 | | 3 | | | 2 | 1 | 2 | | |
| L2 | | | 2 | | | | 1 | | | | 4 | 1 |
| MIR | 1 | | | | | 1 | | | | 1 | | |
| Satellite | | | | 1 | | | | | | | | |
| Simple Repeat | | 1 | | | | 1 | | | | | | |
| hAT-Blackjack | 1 | | | | | | | | | | | |
| hAT-Charlie | | | 1 | 2 | | | | | | 1 | 1 | |

SNP Array Testing for Pre-Implantation Haplotyping.

Figure 9:
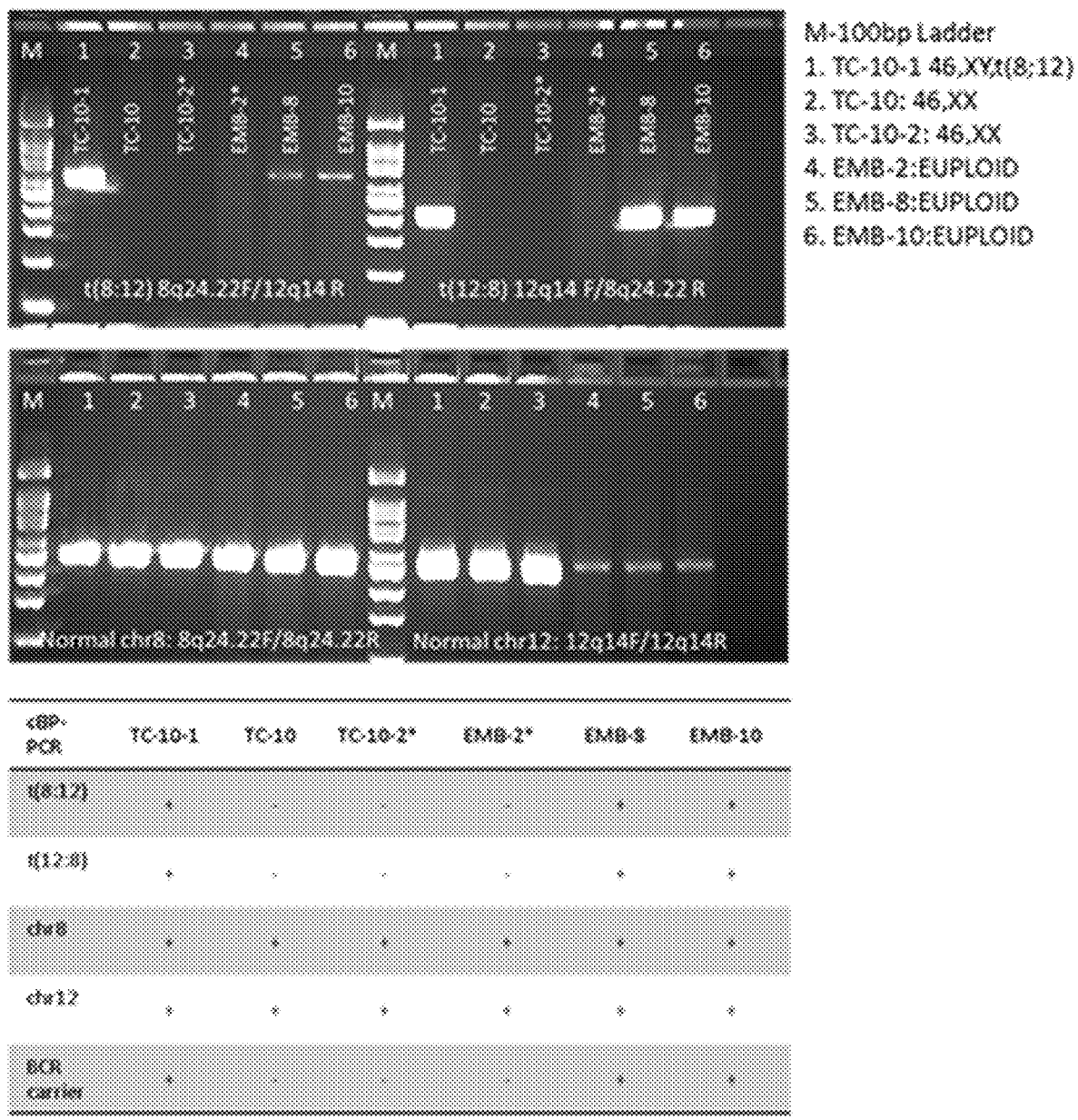
FIG. 9 depicts the result of a custom designed breakpoint PCR using established MINION™ sequencer breakpoint mapping strategy. Breakpoint amplification is present in the parent (TC-10-1) and embryos balanced translocation carriers (EMB-8 and 10), and absent in the parent (TC-10), embryo EMB-2 and child born after transferring this embryo (TC-10-2).
Figure 10:
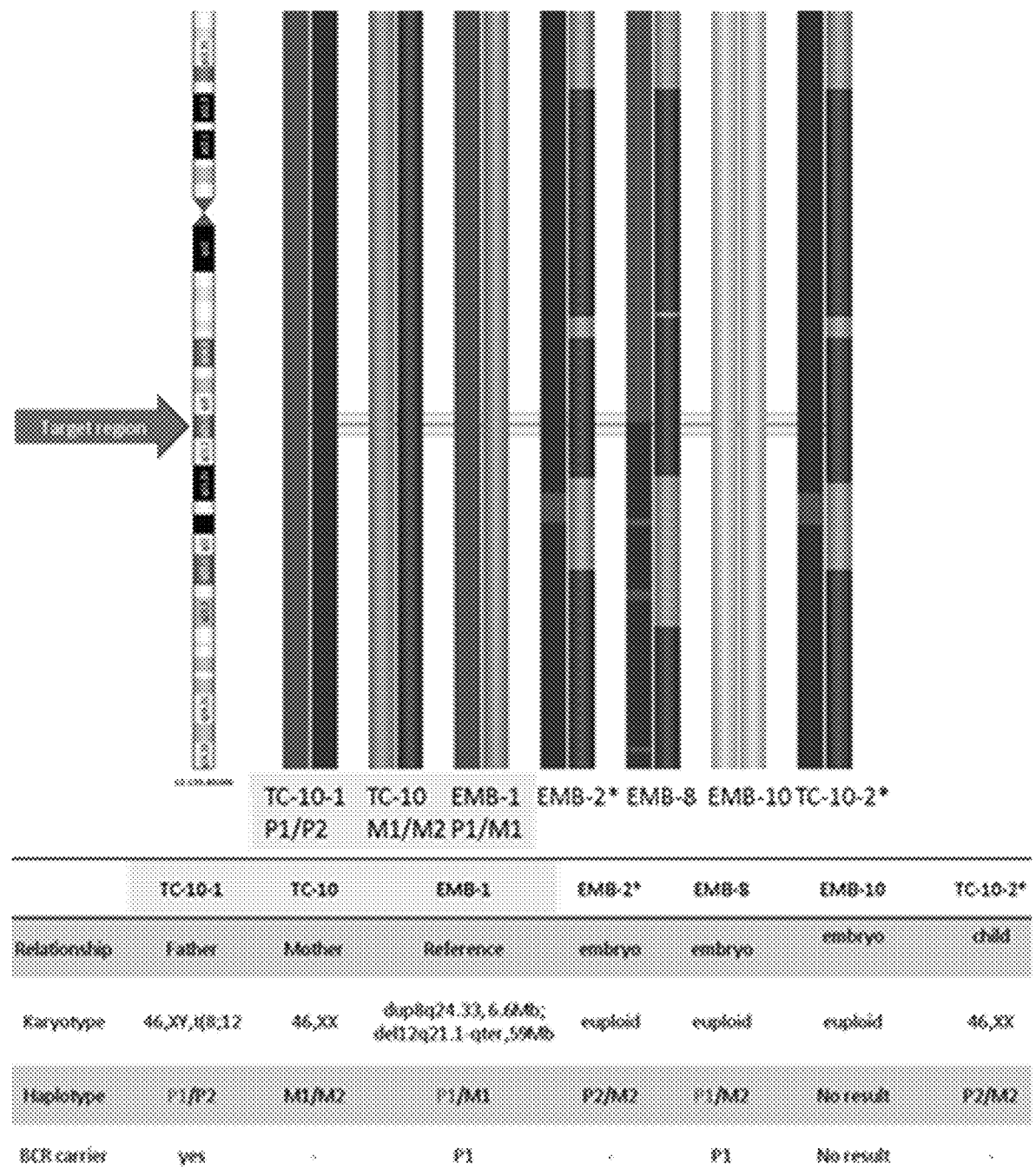
FIG. 10 depicts SNP haplotyping using Karyomapping Infinium Arrays visualized using BlueFuse multi software. Arrow indicates the region of interest that was karyotype guided. EMB-2 inherited normal paternal allele (P2) corresponding to the haplotype and karyotype of the child born after transfer of this embryo.

SNP based genotyping was performed with the Infinium Karyomapping Assay that utilizes the Illumina Human Karyomap-12 V1.0 microarray, as previously described (Handyside et al., 2010). Following manufacturer's protocol technician hands-on time was over 6 hours for a total protocol time of 2 days. Each Karyomap-12 bead chip contained approximately 300,000 SNPs. The analysis was performed using BlueFuse software (Illumina, Calif.) based on informative SNPs in the breakpoint region. SNPs are informative if they are heterozygous in the carrier and homozygous in the partner and should be homozygous in the carrier's parents or other family members. This information was used to determine the carrier's haplotype linked to the derivative chromosome or to the normal chromosome. An affected child or an unbalanced SR embryo was used as a reference. The haplotypes of the whole chromosomes involved in the balanced translocation and the corresponding normal homologous chromosomes could indicate the presence of homologous recombination around the breakpoints. The benchmark to distinguish balanced SR vs. normal embryos combined haplotypes of the breakpoint regions and the presence of homologous recombination in these regions. When the embryo's haplotype was the same as the unbalanced or affected reference samples (in-phase with reference), it was defined as a balanced translocation carrier (FIG. 9 and FIG. 10). However, if the embryo haplotype differed (out-of-phase) from the unbalanced/affected reference sample, it was defined as non-carrier. Prediction of carrier status of an embryo is limited to cases free of recombination in proximity to the breakpoints 10-12.

FIG. 9 and FIG. 10 show concordant results of pre-implantation balanced translocation carrier determination by nanopore sequencing with a MINION™ sequencer and SNP haplotyping. In FIG. 9, results of a custom designed breakpoint PCR using established MINION™ sequencer breakpoint mapping strategy is illustrated. Breakpoint amplification is present in the parent (TC-10-1) and embryos balanced translocation carriers (EMB-8 and 10), and absent in the parent (TC-10), embryo EMB-2 and child born after transferring this embryo (TC-10-2). In FIG. 10, SNP haplotyping using Karyomapping Infinium Arrays visualized using Blue-Fuse multi software is illustrated. Unbalanced embryo from the same IVF cycle was used as reference for haplotype phasing. Paternal haplotype P1 is associated with the rearranged chromosomes. Arrow indicates the region of interest that was karyotype guided. EMB-2 inherited normal paternal allele (P2) corresponds to the haplotype and karyotype of the child born after transfer of this embryo.

Nanopore Long-Read Sequencing can Precisely Determine Breakpoints in Balanced Rearrangements.

Nine known balanced translocation and inversion carriers and 2 suspected balanced translocation carriers were sequenced using our nanopore sequencing cBP-PCR analysis pipeline. Between 2 and 8 derivative reads spanned the breakpoints, with an average read length of 4.5 kb (metrics presented in Table 2). Breakpoints were successfully identified in all cases. The long-read sequencing enabled the determination of the strand orientation after translocation/inversion, which is essential to design the cBP-PCR primers. Table 1 summarizes the location of each rearrangement determined by karyotyping and by long-read sequencing. For all patients, the breakpoints detected by long-read sequencing were within the cytogenetic bands determined by karyotyping. Genomic coordinates of the translocations detected in the two cases with incidental BCR findings (TC9 and TC11) were first identified by sequencing with the MINION™ sequencer and later confirmed by conventional karyotyping and FISH analysis of the parent.

All 22 translocation/inversion breakpoints studied, were located within repeated elements (Table 4 and Table 5).

Table 6 and Table 7 summarize the genes upstream and downstream of the breakpoints. Only one breakpoint (TC11, chr 1) disrupted a gene, DAB1, associated with Spinocerebellar ataxia 37 and Lissencephaly with cerebellar hypoplasia, described in details below.

Sanger sequencing determined the flanking regions of the breakpoint and detected an insertion of a sequence at the breakpoint junctions. Results from the cBP-PCR and Sanger sequencing are shown in FIG. 11 to FIG. 14. Sanger sequencing of the breakpoint junctions revealed small insertions/deletions (1-5 bases) in TC3, TC9, and TC11. Remaining translocations and the two inversions were fully balanced. Each cBP-PCR set was robust and reproducible without allele dropout when tested on low template lymphocyte DNA (5 cell sample) from BCR carriers.

Table 6 and Table 7 show genes within 100 kb of breakpoint sites assessed using USCS genome browser and genomic coordinates determined by sequencing with a MINION™ sequencer of patients carriers of balanced rearrangement, for TC-1 to TC-6 (Table 6) and for TC-6 to TC-11 (Table 7). Gene density within 100 kb of the 22 breakpoints analyzed in the 11 BCR carriers is presented, with the exception of DAB1 in TC-11, the rest of the genes in proximity of the breakpoints were not affected by the translocation however, the possible positional effect on their function was not evaluated.

TABLE 6

Genes within 100 kb of breakpoint sites assessed for TC-1 to TC-6

| TC-1 | TC-2 | TC-3 | TC-4 | TC-5 | TC-6 |
| --- | --- | --- | --- | --- | --- |
| AL118516.1 | AC007878.1 | AL031963.1 | AC118282.1 | AL359881.1 | AC083841.1 |
| TBC1D22A | AL731892.1 | AL031963.2 | AC118282.2 | AL359881.2 | AC083841.2 |
| TBC1D22A-AS1 | CYP4A11 | AL031963.3 | AC118282.3 | AL359881.3 | AC083841.3 |
|  | CYP4B1 | AL133351.1 | AC118282.4 | CAMTA1 | AC083841.4 |
|  | CYP4Z2P | AL133351.4 | MTCO3P39 | LINC01310 | AC090574.1 |
|  | DYSF | AL133351.5 | MTND3P22 | PER3 | CYP11B1 |
|  | RNU6-105P | BPHL | RPS14P7 | UTS2 | CYP11B2 |
|  | ZNF638 | FAM136BP | SNX18P23 | VAMP3 | GML |
|  |  | LINC01011 |  | Z98884.1 | LY6D |
|  |  | MIR7855 |  | Z98884.2 | LYNX1 |
|  |  | NQO2 |  |  | LYPD2 |
|  |  | PLEKHG3 |  |  | PRDM14 |
|  |  | RIPK1 |  |  | RN7SL675P |
|  |  | RNA5SP201 |  |  | RNA5SP270 |
|  |  | SERPINB6 |  |  | RNU1-101P |
|  |  | SERPINB8P1 |  |  | SDCBPP2 |
|  |  | SPTB |  |  | SLURP2 |
|  |  |  |  |  | SUMO2P20 |
|  |  |  |  |  | ZNHIT1P1 |

Table 7 shows genes within 100 kb of breakpoint sites, as assessed for TC-7 to TC-11.

TABLE 7

Genes within 100 kb of breakpoint sites assessed for TC-7 to TC-11

| TC-7 | TC-8 | TC-9 | TC-10 | TC-11 |
|---|---|---|---|---|
| AC007663.1 | CAND1 | AC090198.1 | AC110053.1 | DAB1 |
| AC007663.3 | GGTA2P | AC090922.1 | AC090503.2 | AL390243.1 |
| AC007663.4 | OR10D1P | AP006216.1 | | |
| AC007731.1 | OR10D3 | AP006216.2 | | |
| AC007731.3 | OR10N1P | APOA1 | | |
| AC007731.5 | OR8D1 | APOA1-AS | | |
| AP006216.1 | OR8F1P | APOA4 | | |
| AP006216.2 | OR8G1 | APOA5 | | |
| APOA1 | OR8G2P | APOC3 | | |
| APOA1-AS | OR8G3P | BUD13 | | |
| APOA4 | OR8G5 | MIR6844 | | |
| APOA5 | OR8G7P | MTSS1 | | |
| APOC3 | RAB11AP2 | NDUFB9 | | |
| BUD13 | SLC5A4P1 | RNF139 | | |
| DGCR6L | VWA5A | RNF139-AS1 | | |
| MIR1286 | | SIK3 | | |
| RNU6-225P | | TATDN1 | | |
| RTN4R | | TRMT12 | | |
| SCARF2 | | ZPR1 | | |
| SIK3 | | | | |
| USP41 | | | | |
| ZNF74 | | | | |
| ZPR1 | | | | |

Table 1 provides results of comprehensive whole genome copy number analysis of the embryos and carrier status for the rearrangement, using nanopore sequencing-breakpoint specific cBP-PCR. 55/82 embryos were diagnosed as aneuploid/unbalanced and 27/82 as euploid/balanced. 11 of the 27 euploid embryos were identified as balanced translocation carriers. No embryos were found to show mosaicism in this cohort of embryos. Nine euploid, non-carrier embryos have been transferred to date, of which 5 resulted in healthy live births, 2 in an ongoing pregnancy, 1 in a miscarriage and 1 in no implantation. cBP-PCR, Sanger sequencing and cytogenetic testing on five babies born to date confirmed 100% concordance with preimplantation testing results (see FIG. 9 to FIG. 14).

Figure 11:
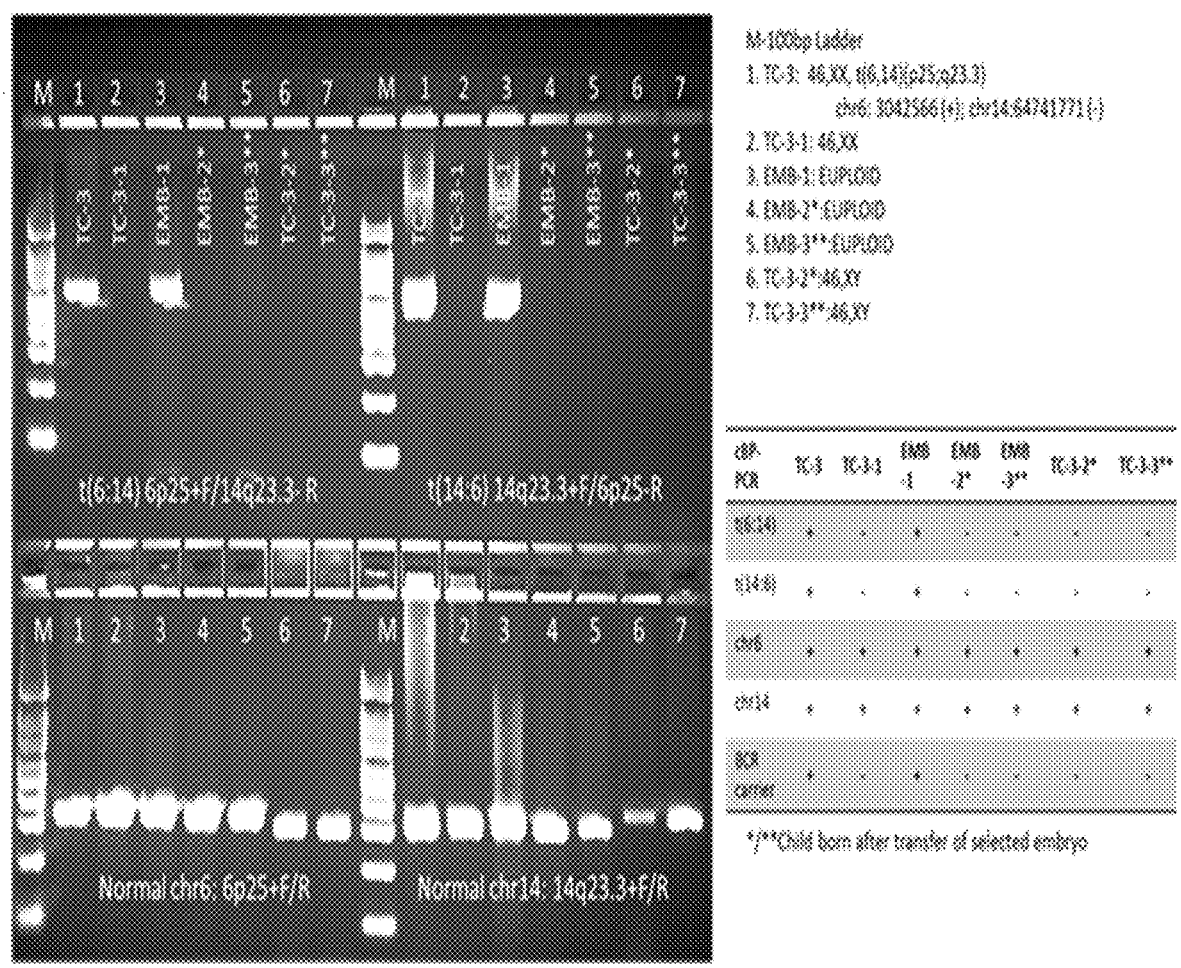
FIG. 11 depicts results from custom breakpoint (cBP) PCR in couple TC-3 undergoing PGT-SR. Comprehensive PGT-SR on the embryos was performed using the assay based on MINION™ sequencer breakpoint mapping of parental samples.
Figure 12:
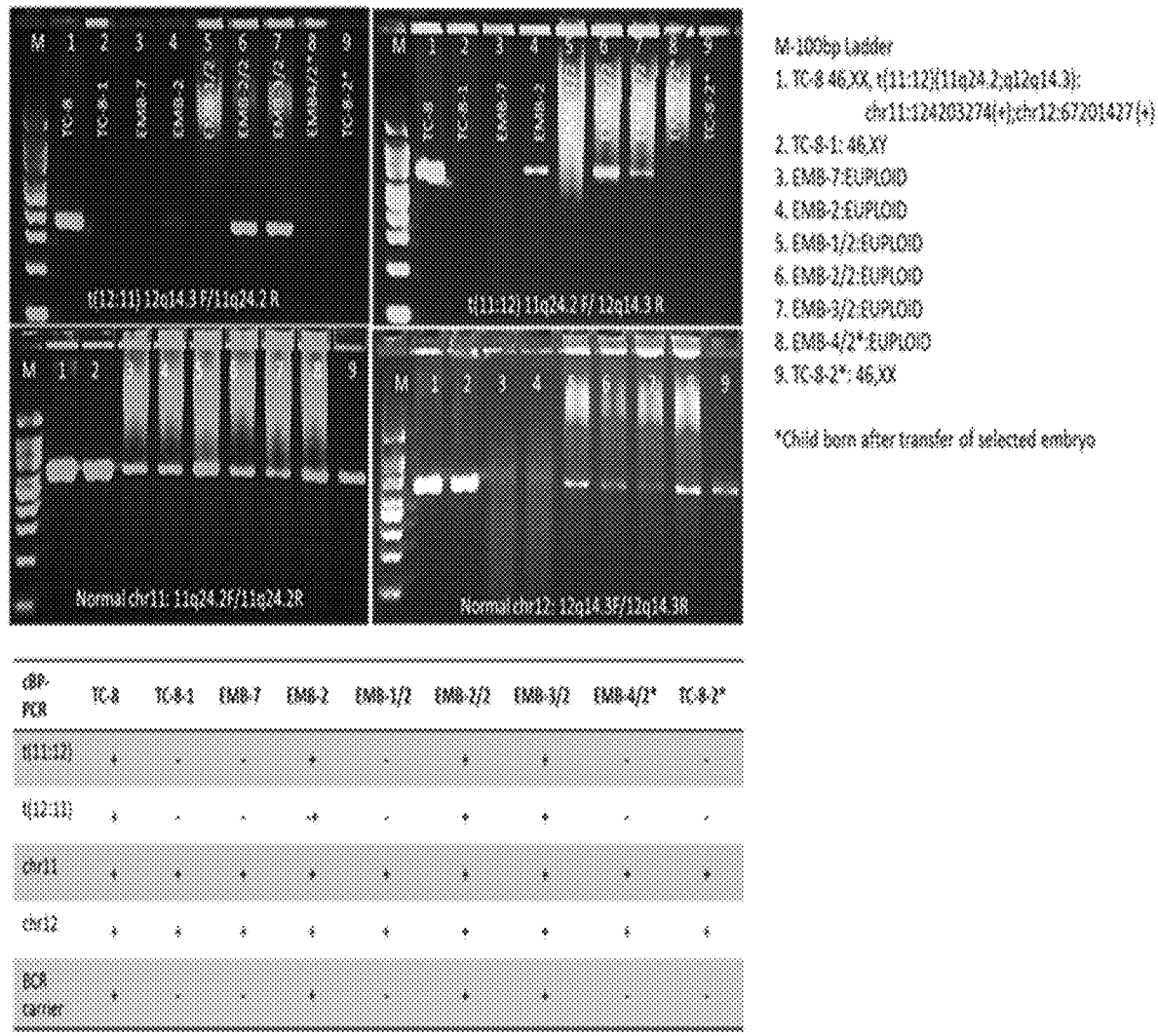
FIG. 12 depicts results from custom breakpoint (cBP) PCR in couple TC-8 undergoing PGT-SR. Comprehensive PGT-SR on the embryos was performed using the assay based on MINION™ sequencer breakpoint mapping of parental samples.

FIG. 11 to FIG. 14 show results from custom breakpoint (cBP) PCR in 3 couples undergoing PGT-SR. Comprehensive PGT-SR on the embryos was performed using the assay based on breakpoint mapping of parental samples using a MINION™ sequencer. FIG. 11 (TC-3) and FIG. 12 (TC-8) show preimplantation and postnatal results from cBP-PCR on children born after embryo transfer are in full concordance.

Figure 13:
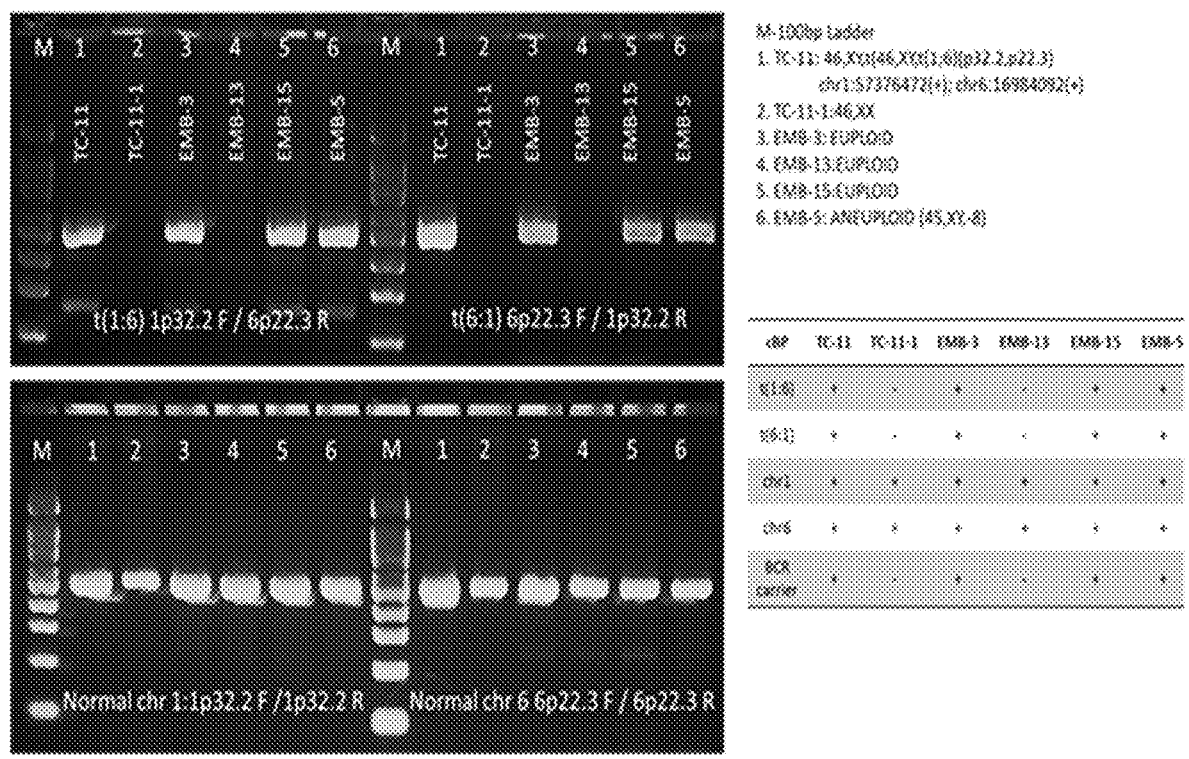
FIG. 13 depicts results from custom breakpoint (cBP) PCR in couple TC-11 undergoing PGT-SR. Comprehensive PGT-SR on the embryos was performed using the assay based on MINION™ sequencer breakpoint mapping of parental samples. Preimplantation and postnatal results from cBP-PCR on child born after embryo transfer is in full concordance.
Figure 14:
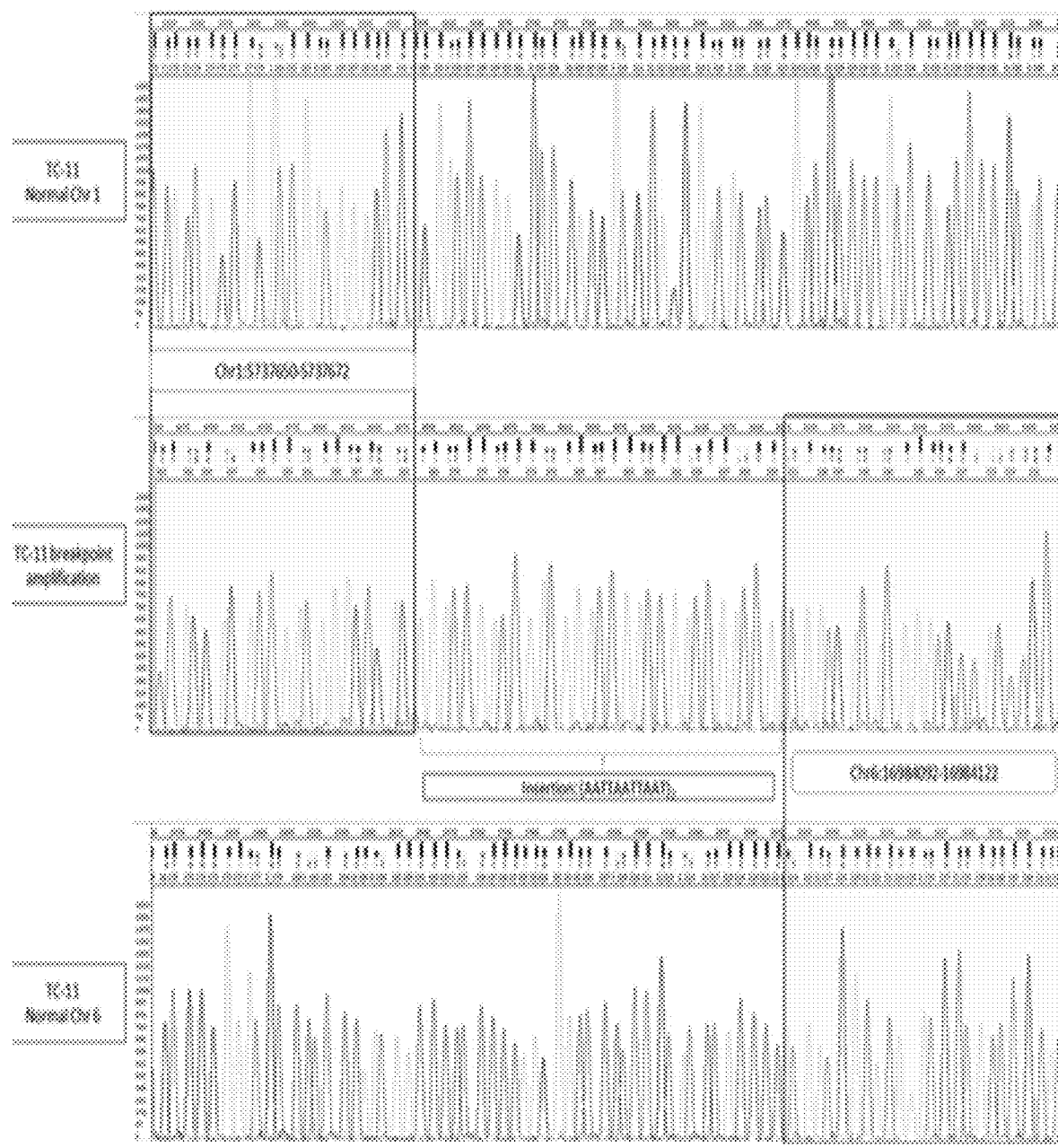
FIG. 14 depicts schematic results from TC-11 (see FIG. 13) of Sanger sequencing of the breakpoints of TC-11, revealing an insertion of 22 bp at junction site, that was transmitted to both embryos balanced translocation carriers (EMB-3 and EMB-15).

In FIG. 13 and FIG. 14, Sanger sequencing of the breakpoints of TC-11 revealed insertion of 22 bp at junction site, that was transmitted to both embryos balanced translocation carriers (EMB-3 and EMB-15). (EMB=embryo, *Postnatal results from a child born after embryo transfer selected with PGT-SR).

Standard Short Read PGT-SR Analysis is not Able to Distinguish BCR Carriers from Non-Carrier Embryos.

All embryos (n=82) from 11 couples with BCR were also tested using standard PGT-SR short read whole genome low pass sequencing to determine if they were abnormal (unbalanced or aneuploid), mosaic or euploid/balanced (Table 1). As discussed above, this approach is not able to distinguish balanced BCR carrier from non-carrier embryos. In addition, the resolution limit of this technique does not allow detection of unbalanced aberrations smaller than 10 Mb. For case TC-1 (46,XX,t(8:22)(q24.3,q13.33), with a history of 4 miscarriages and an affected child with Phelan-McDermid Syndrome (22q13 deletion, [arr[hg19]:8q24.3 (140,366, 315-146,295,771)x3, 22q13.31q13.33 (47,254,703-51,176, 099)x1]), short read sequencing failed to detect the Adjacent-1 unbalanced segregation. The application of a diagnostic strategy for comprehensive PGT-SR using nanopore sequencing is described in detail in FIG. 15 and FIG. 16. This strategy is applicable to the couple described as TC-1.

Standard NGS-based PGT-SR diagnosed 3 of the embryos to be balanced/euploid (EMB 2: 46,XX,3: 46,XX and 5: 46,XX) and one aneuploid (EMB 6: 48,XY,+16,+21). Nanopore-based CNV analysis produced identical results and identified EMB 2 as euploid (46,XX) and EMB 6 as aneuploid (48,XY,+16,+21, del 8q24.3, dup22q13.31). cBP PCR determined that 1 of the 3 euploid embryos was a balanced carrier (EMB 2 46,XX, t(8,22)(q24.3,q13.31)), and the other 2 (EMB 3 and 5, 46,XX) were non-carriers. EMB 6 in addition to the trisomy 16 and 21 had inherited an unbalanced translocation resulting in deletion of chr8q24.3 and duplication of 22q13.31 (see FIG. 7 and FIG. 8).

Figure 15:
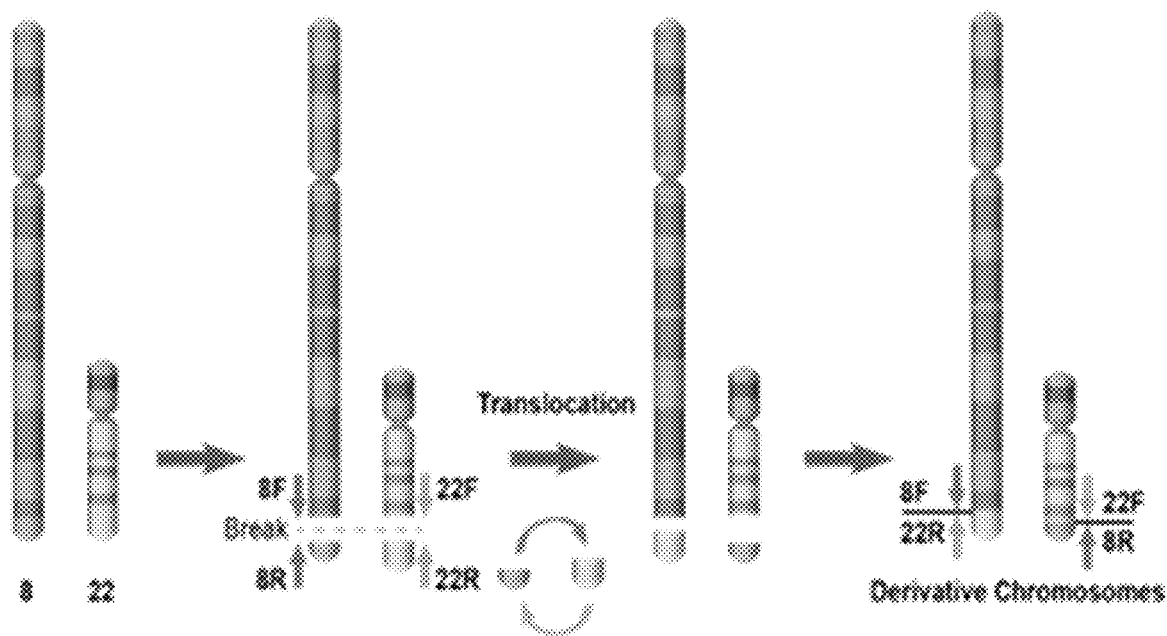
FIG. 15 pertains to translocation of chr 8 and chr 22, and provides a schematic of a diagnostic strategy for comprehensive PGT-SR utilizing nanopore sequencing.
Figure 16:
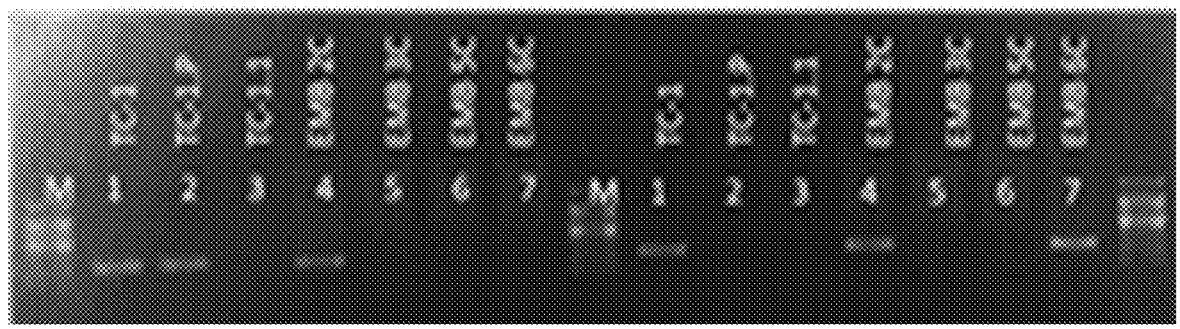
FIG. 16 shows custom breakpoint amplification for use in the diagnostic strategy for comprehensive PGT-SR utilizing nanopore sequencing. Standard NGS-based PGT-SR diagnosed 3 of the embryos to be balanced/euploid (EMB 2: 46,XX, 3: 46,XX and 5: 46,XX) and one aneuploid (EMB 6: 48,XY,+16,+21). cBP PCR determined that 1 of the 3 euploid embryos was a balanced carrier (EMB 2 46,XX, t(8,22)(q24.3,q13.31)), and the other 2 (EMB 3 and 5, 46,XX) were non-carriers.
Figure 16:
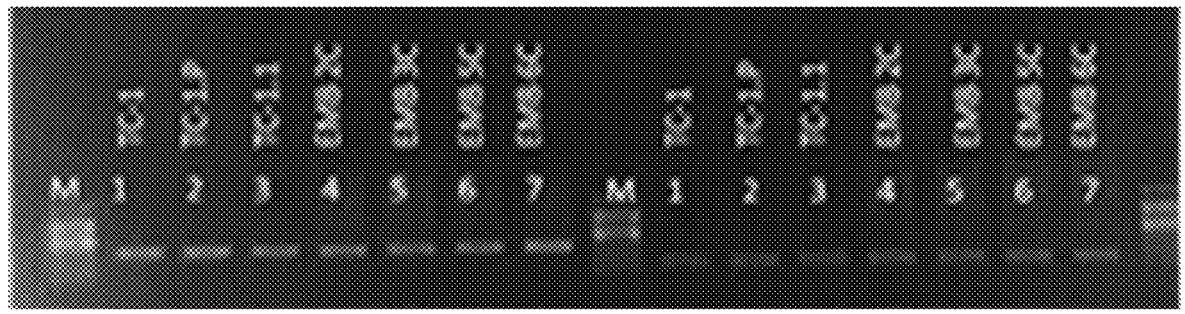
Figure 17:
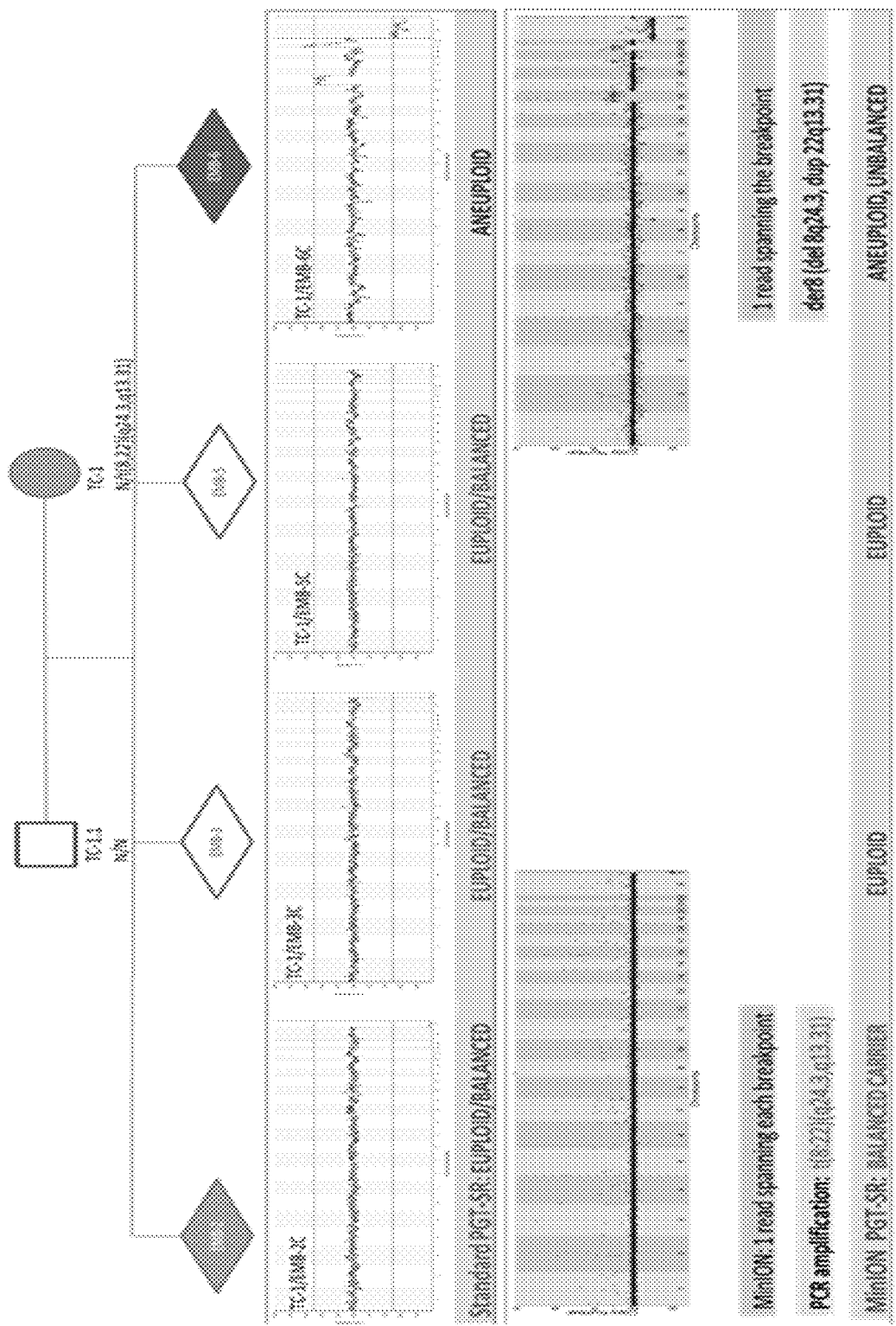
FIG. 17 depicts a schematic overview of the testing of TC-1 embryos in the identification of one of the 3 euploid embryos as a balanced carrier.

The Sanger sequencing single base resolution pertaining to data presented in FIG. 15 to FIG. 17 involved the following:

Normal chr 22, amplification primer set 22F/22R, chr22: 46851962+46852103 (142 bp), Chr 22 breakpoint 46,852,062;

Normal chr 8, amplification primer set 8F/8R, chr8: 139353389+139353718 (330 bp), Chr 8 breakpoint 139,353,588; and Derivative t(22:8) amplification primer set 22F/8R, chr22: 46851962+46852062: chr8:139353588+139353718 (t(22:8)(46852,062:139,353,588).

SNP array haplotyping and nanopore-based balanced translocation carrier discrimination showed full concordance. SNP array haplotyping was performed using a 5 Mb region around the breakpoint as described previously (Treff et al., 2016; Zhang et al., 2017). Breakpoint location for each BCR determined by nanopore sequencing was utilized to define the region needed to derive the haplotype associated with each translocation. DNA from the affected child of TC-1 and all unbalanced embryos from the remaining patients were used as references to map the rearranged chromosomes. The results regarding embryo carrier status that were determined by nanopore sequencing and cBP-PCR were fully concordant with haplotype segregation analysis of SNP arrays.

Gene Disruption by Translocation.

Breakpoints associated with balanced translocation of patient TC-11 t(1:6), disrupted intron 1 of DAB1 gene (Chr 1: 56,994,778-58,546,734 reverse strand, GRCh38: CM000663.2, OMIM #615945: Spinocerebellar ataxia 37, autosomal dominant inheritance). The gene is part of the reelin (RELN; OMIM 600514) signaling pathway that plays a critical role in the correct positioning of neurons within the developing brain. DAB1 serves as an intracellular adaptor that is tyrosine phosphorylated when reelin binds to the lipoprotein receptors VLDLR and APOER2 (LRP8) on the surface of neurons as shown in animal studies (Huang et al., 2005). DAB1 has complex expression because it contains several alternative first exons that can result in transcripts with variable 5-prime UTRs (Seixas et al., 2017). Various transcripts were found in multiple human central nervous system regions, including the cerebellum, and all showed higher expression in human fetal brain tissue compared to adult brain. DAB1 gene spans more than 1.2 Mb where exons 2 through 14 span more than 294 kb and contain the coding region for the major DAB1 isoform (Bar et al., 2003). Exon 15 contains the 3-prime UTR. Multiple 5-prime exons are spread over a 961-kb region and produce 6 alternative 5-prime UTRs. The most complex 5-prime UTR, UTR 1B, is made up of 7 exons.

The breakpoint on chr 1 of TC11 disrupts the gene however because of the complex expression and usually not translated exon 1 this patient has no phenotype associated with spinocerebellar ataxia.

Conclusion

These data illustrate that the comprehensive method described herein can discriminate between euploid BCR carrier and non-carrier embryos by accurate delineation of the chromosomal rearrangement in parent BCR carriers. A preimplantation test to determine translocation carriers can be used to the benefit of those pursuing reproductive technologies.

Examples Only

In the preceding description, for purposes of explanation, numerous details are set forth in order to provide a thorough understanding of the embodiments. However, it will be apparent to one skilled in the art that these specific details are not required.

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

References

All publications, patents and patent applications mentioned in this specification are indicative of the level of skill those skilled in the art to which this invention pertains and are herein incorporated by reference to the same extent as if each individual publication, patent, or patent application was specifically and individually indicated to be incorporated by reference.

Aristidou C, Koufaris C, Theodosiou A, et al. (2017) Accurate breakpoint mapping in apparently balanced translocation families with discordant phenotypes using whole genome mate-pair sequencing. *PLoS One* 12(1), e0169935.

Bar I, Tissir F, Lambert de Rouvroit C, De Backer O, Goffinet A M (2003). The gene encoding disabled-1 (DAB1), the intracellular adaptor of the Reelin pathway, reveals unusual complexity in human and mouse. *The Journal of biological chemistry* 278, 5802-12.

Cretu Stancu M, van Roosmalen M J, Renkens I, et al. (2017) Map-ping and phasing of structural variation in patient genomes using nanopore sequencing. *Nat Commun* 8, 1326.

Darwish, E. & Magdi, Y. Artificial shrinkage of blastocoel using a laser pulse prior to vitrification improves clinical outcome. *Journal of assisted reproduction and genetics* 33, 467-471, doi:10.1007/510815-016-0662-z (2016).

Garvin T, Aboukhalil R, Kendall J, et al. (2015) Interactive analysis and assessment of single-cell copy-number variations. *Nature methods* 12, 1058-60.

Halgren C, Nielsen N M, Nazaryan-Petersen L, et al. (2018) Risks and recommendations in prenatally detected de novo balanced chromosomal rearrangements from assessment of long-term outcomes. *Am J Hum Genet* 102, 1090-103.

Handyside A H, Harton G L, Mariani B, et al. (2010) Karyomapping: a universal method for genome wide analysis of genetic disease based on mapping crossovers between parental haplotypes. *Journal of medical genetics* 47, 651-8.

Huang Y, Shah V, Liu T, Keshvara L. (2005) Signaling through Disabled 1 requires phosphoinositide binding. *Biochemical and biophysical research communications* 331, 1460-8.

Li H. (2018) Minimap2: pairwise alignment for nucleotide sequences. *Bioinformatics* (Oxford, England) 34, 3094-100.

Li H, Handsaker B, Wysoker A, et al. (2009) The Sequence Alignment/Map format and SAMtools. *Bioinformatics* (Oxford, England) 25, 2078-9.

Madjunkova S et al. Non-invasive preimplantation genetic testing for monogenetic diseases and aneuploidies using cell free embryonic DNA, in: *American Society of Human Genetics 68th Annual Meeting, San Diego*, p 1270, Abstract 3007T (2018).

Munné S, Sandalinas M, Escudero T, Fung J, Gianaroli L, Cohen J. (2000) Outcome of preimplantation genetic diagnosis of translocations. *Fertil Steril* 73, 1209-18.

Seixas A I, Loureiro J R, Costa C, et al. (2017) A Pentanucleotide ATTTC Repeat Insertion in the Non-coding Region of DAB1, Mapping to SCA37, Causes Spinocerebellar Ataxia. *American journal of human genetics* 101, 87-103.

Tan Y Q, Tan K, Zhang S P, et al. (2013) Single-nucleotide polymorphism microarray-based preimplantation genetic diagnosis is likely to improve the clinical outcome for translocation carriers. *Human reproduction* (Oxford, England) 28, 2581-92.

Treff N R, Thompson K, Rafizadeh M, et al. (2016) SNP array-based analyses of unbalanced embryos as a reference to distinguish between balanced translocation carrier and normal blastocysts. *Journal of assisted reproduction and genetics* 33, 1115-9.

Untergasser A, Cutcutache I, Koressaar T, et al. (2012) Primer3—new capabilities and interfaces. *Nucleic acids research* 40, e115.

Vermeesch J R, Voet T, Devriendt K. (2016) Prenatal and pre-implantation genetic diagnosis. *Nat Rev Genet* 17, 643-56.

Wang L, Shen J, Cram D S, et al. (2017) Preferential selection and transfer of euploid noncarrier embryos in preimplantation genetic diagnosis cycles for reciprocal translocations. *Fertility and sterility* 108, 620-7.e4.

Wei S, Weiss Z R, Gaur P, Forman E, Williams Z. (2018) Rapid preimplantation genetic screening using a handheld, nanopore-based DNA sequencer. *Fertility and sterility* 110, 910-6.e2.

Zhang S, Lei C, Wu J, et al. (2017) The establishment and application of preimplantation genetic haplotyping in embryo diagnosis for reciprocal and Robertsonian translocation carriers. *BMC medical genomics* 10, 60.

The invention claimed is:

1. A method of determining carrier status of an embryo for a balanced chromosomal rearrangement (BCR) prior to implantation of the embryo, said method comprising:
   obtaining cells of the embryo from a trophectoderm biopsy at least day 4 post in vitro fertilization;
   conducting long-read nanopore sequencing and data analysis of the DNA of the cells and the DNA of the parent carrier of BCR to detect at least one breakpoint, wherein the sequencing is conducted on DNA fragments prepared from the DNA of the parent carrier of BCR and from the DNA of the cells, wherein said DNA fragments comprise ultra long fragments of 50 kb or greater, and said DNA fragments comprise an average fragment length of from about 5 to 15 kb, wherein the BCR of the parent carrier comprises a Robertsonian translocation;
   preparing customized primers specific to the breakpoint;
   employing the customized primers in a polymerase chain reaction customized to the breakpoint (cBP-PCR) to determine whether the breakpoint is indicative of BCR;
   determining on the basis of cBP-PCR whether the embryo status is BCR carrier or BCR noncarrier; and
   determining, on the basis of Sanger sequencing, whether the BCR carrier embryo is fully balanced.

2. The method of claim 1, wherein the cells from trophectoderm biopsy comprise 3 to 10 trophectoderm cells.

3. The method of claim 1, wherein the cells are obtained from the embryo at day 5 or 6 post in vitro fertilization.

4. The method of claim 1, wherein in the step of conducting long-read nanopore sequencing, the DNA fragments are prepared and sequenced having an average length of from about 8 to 10 kb.

5. The method of claim 1, wherein in the step of conducting long-read nanopore sequencing, the DNA fragments are prepared and sequenced comprising ultra long fragments of 100 kb or greater.

6. The method of claim 1, wherein the long-read nanopore sequencing is conducted using a real-time long-read nucleic acid sequencer for up to 48 hours.

7. The method of claim 6, wherein a chromosomal copy-number variation (CNV) plot is generated from the long-read nanopore sequencing.

8. The method of claim 1, wherein multiple breakpoints are detected, and wherein customized primers are prepared for each breakpoint.

9. The method of claim 1, wherein the Sanger sequencing is conducted to determine full balance at single base resolution.

10. The method of claim 1, wherein the breakpoint is detected in a highly repetitive genomic region.

11. The method of claim 1, further comprising implantation of the embryo into a human subject if BCR noncarrier status is indicated.

12. The method of claim 1, further comprising the step of freezing the embryo if BCR noncarrier status is indicated.

13. The method of claim 12, further comprising the step of thawing the frozen embryo and implanting said embryo into a human subject.

* * * * *